(12) United States Patent
Aronov et al.

(10) Patent No.: US 8,524,906 B2
(45) Date of Patent: Sep. 3, 2013

(54) TETRAHYDROTHIAZOLOPYRIDINE INHIBITORS OF PHOSPHATIDYLINOSITOL 3-KINASE

(75) Inventors: Alex Aronov, Newton, MA (US); Upul Keerthi Bandarage, Lexington, MA (US); Kevin Michael Cottrell, Cambridge, MA (US); Robert J. Davies, Arlington, MA (US); Elaine B. Krueger, Milton, MA (US); Mark Willem Ledeboer, Acton, MA (US); Brian Ledford, Norton, MA (US); Arnaud Le Tiran, Croissy sur Seine (FR); David Messersmith, Somerville, MA (US); Tiansheng Wang, Concord, MA (US); Jinwang Xu, Framingham, MA (US); Yusheng Liao, Lexington, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 13/211,502

(22) Filed: Aug. 17, 2011

(65) Prior Publication Data
US 2012/0039849 A1     Feb. 16, 2012

Related U.S. Application Data

(63) Continuation of application No. PCT/US2010/024323, filed on Feb. 16, 2010.

(60) Provisional application No. 61/153,056, filed on Feb. 17, 2009.

(51) Int. Cl.
*A61K 31/4365* (2006.01)
*C07D 513/04* (2006.01)

(52) U.S. Cl.
USPC .......................................... 546/114; 514/301

(58) Field of Classification Search
USPC ........................................ 546/114; 514/301
See application file for complete search history.

(56) References Cited

FOREIGN PATENT DOCUMENTS

| WO | 2007095588 A1 | 8/2007 |
|----|---------------|--------|
| WO | 2008001076 A1 | 1/2008 |
| WO | 2010002458 A1 | 3/2010 |

OTHER PUBLICATIONS

Georg Pilz, "Modern multiple sclerosis treatment—what is approved, what is on the horizon" Drug Discovery Today Dec. 2008, vol. 13, Nos. 23/24 1013-1025.*
Romina Marone "Targeting phosphoinositide 3-kinase—Moving towards therapy" Biochimica et Biophysica Acta 2008, 1784, 159-185.*
Teahter J. Sundstrom et al., "Inhibitors of phosphoinositide-3-kinase: a structure-based approach to understanding potency and selectivity"; Organic & Biomolecular Chemistry, 2009, 7, 840-850.

* cited by examiner

*Primary Examiner* — David K O Dell
(74) *Attorney, Agent, or Firm* — Daniel A. Pearson

(57) ABSTRACT

The present invention relates to compounds useful as inhibitors of PI3K, particularly of PI3Kγ. The invention also provides pharmaceutically acceptable compositions comprising said compounds and methods of using the compositions in the treatment of various disease, conditions, or disorders.

14 Claims, No Drawings

TETRAHYDROTHIAZOLOPYRIDINE INHIBITORS OF PHOSPHATIDYLINOSITOL 3-KINASE

CROSS-REFERENCE TO RELATED APPLICATIONS

This application is a continuation of International Patent Application No. PCT/US2010/024323, filed Feb. 16, 2010, which claims benefit, under 35 U.S.C. §119, to U.S. Provisional Application No. 61/153,056 filed Feb. 17, 2009, the entire disclosures of which are incorporated herein by reference.

TECHNICAL FIELD OF THE INVENTION

The present invention relates to compounds useful as inhibitors of phosphatidylinositol 3-kinase (PI3K). The invention also provides pharmaceutically acceptable compositions comprising the compounds of the invention and methods of using the compositions in the treatment of various disorders.

BACKGROUND OF THE INVENTION

PI3Ks are a family of lipid kinases that catalyze the phosphorylation of the membrane lipid phosphatidylinositol (PI) on the 3'-OH of the inositol ring to produce PI 3-phosphate [PI(3)P, PIP], PI 3,4-bisphosphate [PI(3,4)$P_2$, PIP2] and PI 3,4,5-trisphosphate [PI(3,4,5)$P_3$, PIP3]. PI(3,4)$P_2$ and PI(3,4,5)$P_3$ act as recruitment sites for various intracellular signaling proteins, which in turn form signaling complexes to relay extracellular signals to the cytoplasmic face of the plasma membrane.

Eight mammalian PI3Ks have been identified so far, including four class I PI3Ks. Class Ia includes PI3Kα, PI3Kβ and PI3Kδ. All of the class Ia enzymes are heterodimeric complexes comprising a catalytic subunit (p110α, p110β or p110δ) associated with an SH2 domain-containing p85 adapter subunit. Class Ia PI3Ks are activated through tyrosine kinase signaling and are involved in cell proliferation and survival. PI3Kα and PI3Kβ have also been implicated in tumorigenesis in a variety of human cancers. Thus, pharmacological inhibitors of PI3Kα and PI3Kβ are useful for treating various types of cancer.

PI3Kγ, the only member of the Class Ib PI3Ks, consists of a catalytic subunit p110γ, which is associated with a p101 regulatory subunit. PI3Kγ is regulated by G protein-coupled receptors (GPCRs) via association with βγ subunits of heterotrimeric G proteins. PI3Kγ is expressed primarily in hematopoietic cells and cardiomyocytes and is involved in inflammation and mast cell function. Thus, pharmacological inhibitors of PI3Kγ are useful for treating a variety of inflammatory diseases, allergies and cardiovascular diseases.

Although a number of PI3K inhibitors have been developed, there is a need for additional compounds to inhibit PI3Ks for treating various disorders and diseases, such as autoimmune diseases, inflammatory diseases, cancer, allergic diseases, asthma, and respiratory diseases. Accordingly, it would be desirable to develop additional compounds that are useful as inhibitors of PI3K.

SUMMARY OF THE INVENTION

It has been found that compounds of this invention, and pharmaceutically acceptable compositions thereof, are effective as inhibitors of PI3K, particularly PI3Kγ. Accordingly, the invention features compounds having the general formula:

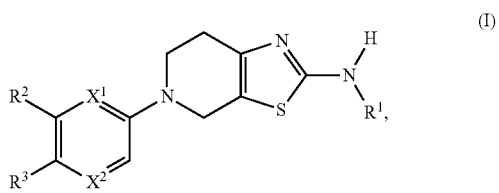

or a pharmaceutically acceptable salt thereof, where each of $R^1$, $R^2$, $R^3$, $X^1$, and $X^2$ is as defined herein.

The invention also provides pharmaceutical compositions that include a compound of formula I and a pharmaceutically acceptable carrier, adjuvant, or vehicle. These compounds and pharmaceutical compositions are useful for treating or lessening the severity of a variety of disorders, including autoimmune diseases and inflammatory diseases of the CNS.

The compounds and compositions provided by this invention are also useful for the study of PI3K in biological and pathological phenomena; the study of intracellular signal transduction pathways mediated by such kinases; and the comparative evaluation of new kinase inhibitors.

DETAILED DESCRIPTION OF THE INVENTION

Definitions and General Terminology

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry," Thomas Sorrell, University Science Books, Sausalito: 1999, and "March's Advanced Organic Chemistry," 5th Ed., Smith, M. B. and March, J., eds. John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted," whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

As described herein, when the term "optionally substituted" precedes a list, said term refers to all of the subsequent substitutable groups in that list. For example, if X is halogen; optionally substituted $C_{1-3}$ alkyl or phenyl; X may be either optionally substituted alkyl or optionally substituted phenyl. Likewise, if the term "optionally substituted" follows a list, said term also refers to all of the substitutable groups in the prior list unless otherwise indicated. For example: if X is halogen, $C_{1-3}$ alkyl, or phenyl, wherein X is optionally substituted by $J^X$, then both $C_{1-3}$ alkyl and phenyl may be optionally substituted by $J^X$. As is apparent to one having ordinary skill in the art, groups such as H, halogen, $NO_2$, CN, $NH_2$, OH, or $OCF_3$ would not be included because they are not substitutable groups. If a substituent radical or structure is not identified or defined as "optionally substituted," the substituent radical or structure is unsubstituted.

Combinations of substituents envisioned by this invention are preferably those that result in the formation of stable or chemically feasible compounds. The term "stable," as used herein, refers to compounds that are not substantially altered when subjected to conditions to allow for their production, detection, and, preferably, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group," as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments, aliphatic groups contain 1-4 carbon atoms. Suitable aliphatic groups include, but are not limited to, linear or branched, substituted or unsubstituted alkyl, alkenyl, or alkynyl groups. Further examples of aliphatic groups include methyl, ethyl, propyl, butyl, isopropyl, isobutyl, vinyl, and sec-butyl. The terms "alkyl" and the prefix "alk-," as used herein, are inclusive of both straight chain and branched saturated carbon chain. The term "alkylene," as used herein, represents a saturated divalent straight or branched chain hydrocarbon group and is exemplified by methylene, ethylene, isopropylene and the like. The term "alkylidene," as used herein, represents a divalent straight chain alkyl linking group. The term "alkenyl," as used herein, represents monovalent straight or branched chain hydrocarbon group containing one or more carbon-carbon double bonds. The term "alkynyl," as used herein, represents a monovalent straight or branched chain hydrocarbon group containing one or more carbon-carbon triple bonds.

The term "cycloaliphatic" (or "carbocycle") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule, and wherein any individual ring in said bicyclic ring system has 3-7 members. Suitable cycloaliphatic groups include, but are not limited to, cycloalkyl, cycloalkenyl, and cycloalkynyl. Further examples of aliphatic groups include cyclopentyl, cyclopentenyl, cyclohexyl, cyclohexenyl, cycloheptyl, and cycloheptenyl.

The term "heterocycle," "heterocyclyl," "heterocycloaliphatic," or "heterocyclic" as used herein refers to a monocyclic, bicyclic, or tricyclic ring system in which at least one ring in the system contains one or more heteroatoms, which is the same or different, and that is completely saturated or that contains one or more units of unsaturation, but which is not aromatic, and that has a single point of attachment to the rest of the molecule. In some embodiments, the "heterocycle," "heterocyclyl," "heterocycloaliphatic," or "heterocyclic" group has three to fourteen ring members in which one or more ring members is a heteroatom independently selected from oxygen, sulfur, nitrogen, or phosphorus, and each ring in the system contains 3 to 8 ring members.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydroimidazol-2-one.

The term "heteroatom" means one or more of oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or $NR^+$ (as in N-substituted pyrrolidinyl).

The term "unsaturated," as used herein, means that a moiety has one or more units of unsaturation.

The term "alkoxy," or "thioalkyl," as used herein, refers to an alkyl group, as previously defined, attached to the principal carbon chain through an oxygen ("alkoxy") or sulfur ("thioalkyl") atom.

The terms "haloalkyl," "haloalkenyl," and "haloalkoxy" mean alkyl, alkenyl, or alkoxy, as the case may be, substituted with one or more halogen atoms. The term "halogen" means F, Cl, Br, or I.

The term "aryl" used alone or as part of a larger moiety as in "aralkyl," "aralkoxy," or "aryloxyalkyl," refers to a monocyclic, bicyclic, or tricyclic carbocyclic ring system having a total of six to fourteen ring members, wherein said ring system has a single point of attachment to the rest of the molecule, at least one ring in the system is aromatic and wherein each ring in the system contains 3 to 7 ring members. The term "aryl" may be used interchangeably with the term "aryl ring." Examples of aryl rings include phenyl, naphthyl, and anthracene.

The term "heteroaryl," used alone or as part of a larger moiety as in "heteroaralkyl," or "heteroarylalkoxy," refers to a monocyclic, bicyclic, and tricyclic ring system having a total of five to fourteen ring members, wherein said ring system has a single point of attachment to the rest of the molecule, at least one ring in the system is aromatic, at least one ring in the system contains one or more heteroatoms independently selected from nitrogen, oxygen, sulfur or phosphorus, and wherein each ring in the system contains 3 to 7 ring members. The term "heteroaryl" may be used interchangeably with the term "heteroaryl ring" or the term "heteroaromatic."

Further examples of heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

In some embodiments, an aryl (including aralkyl, aralkoxy, aryloxyalkyl, and the like) or heteroaryl (including heteroaralkyl, heteroarylalkoxy, and the like) group may contain one or more substituents. Suitable substituents on the unsaturated carbon atom of an aryl or heteroaryl group include: halogen; —R°; —OR°; —SR°; 1,2-methylenedioxy; 1,2-ethylenedioxy; phenyl (Ph), optionally substituted with R°; —O(Ph), optionally substituted with R°; —(CH$_2$)$_{1-2}$(Ph), optionally substituted with R°; —CH=CH(Ph), optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°C(O)OR°; —NR°NR°C(O)R°; —NR°NR°C(O)N(R°)$_2$; —NR°NR°C(O)OR°; —C(O)C(O)R°; —C(O)CH$_2$C(O)R°; —C(O)OR°; —C(O)R°; —C(S)R°; —C(O)N(R°)$_2$; —C(S)N(R°)$_2$; —B(OR°)$_2$; —OC(O)N(R°)$_2$; —OC(O)R°; —C(O)N(OR°)R°; —C(NOR°)R°; —S(O)$_2$R°; —S(O)$_3$R°; —S(O)$_2$N(R°)$_2$; —S(O)R°; —NR°S(O)$_2$N(R°)$_2$; —NR°S(O)$_2$R°; —N(OR°)R°; —C(=NH)—N(R°)$_2$; —(CH$_2$)$_{0-2}$NHC(O)R°; -L-R°; -L-N(R°)$_2$; -L-SR°; -L-OR°; -L-(C$_{3-10}$ cycloaliphatic), -L-(C$_{6-10}$ aryl), -L-(5-10 membered heteroaryl), -L-(5-10 membered heterocyclyl), oxo, C$_{1-4}$ haloalkoxy, C$_{1-4}$ haloalkyl, -L-NO$_2$, -L-CN, -L-OH, -L-CF$_3$; or two substituents, on the same carbon or on different carbons, together with the carbon or intervening carbons to which they are bound, form a 5-7 membered saturated, unsaturated, or partially saturated ring, wherein L is a C$_{1-6}$ alkylene group in which up to three methylene units are replaced by —NH—, —NR°—, —O—, —S—, —C(O)O—, —OC(O)—, —C(O)CO—, —C(O)—, —C(O)NH—, —C(O)NR°—, —C(=N—CN), —NHCO—, —NR°CO—, —NHC(O)O—, —NR°C(O)O—, —S(O)$_2$NH—, —S(O)$_2$NR°—, —NHS(O)$_2$—, —NR°S(O)$_2$—, —NHC(O)NH—, —NR°C(O)NH—, —NHC(O)NR°—, —NR°C(O)NR°, —OC(O)NH—, —OC(O)NR°—, —NHS(O)$_2$NH—, —NR°S(O)$_2$NH—, —NHS(O)$_2$NR°—, —NR°S(O)$_2$NR°—, —S(O)—, or —S(O)$_2$—, and wherein each occurrence of R° is independently selected from hydrogen, optionally substituted C$_{1-6}$ aliphatic, an unsubstituted 5 to 6 membered heteroaryl or heterocyclic ring, phenyl, or —CH$_2$(Ph), or, two independent occurrences of R°, on the same substituent or different substituents, taken together with the atom(s) to which each R° group is bound, form a 5-8-membered heterocyclyl, aryl, or heteroaryl ring or a 3- to 8-membered cycloalkyl ring, wherein said heteroaryl or heterocyclyl ring has 1 to 3 heteroatoms independently selected from nitrogen, oxygen, or sulfur. Non-limiting optional substituents on the aliphatic group of R° include —NH$_2$, —NH(C$_{1-4}$ aliphatic), —N(C$_{1-4}$ aliphatic)$_2$, halogen, C$_{1-4}$ aliphatic, —OH, —O(C$_{1-4}$ aliphatic), —NO$_2$, —CN, —C(O)OH, —C(O)O(C$_{1-4}$ aliphatic), —O(haloC$_{1-4}$ aliphatic), or haloC$_{1-4}$ aliphatic, wherein each of the foregoing C$_{1-4}$ aliphatic groups of R° is unsubstituted.

In some embodiments, an aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHC(O)O(alkyl), =NNHS(O)$_2$(alkyl), or =NR*, where each R* is independently selected from hydrogen or an optionally substituted C$_{1-8}$ aliphatic. Optional substituents on the aliphatic group of R* are selected from —NH$_2$, —NH(C$_{1-4}$ aliphatic), —N(C$_{1-4}$ aliphatic)$_2$, halogen, C$_{1-4}$ aliphatic, —OH, —O(C$_{1-4}$ aliphatic), —NO$_2$, —CN, —C(O)OH, —C(O)O(C$_{1-4}$ aliphatic), —C(O)NH$_2$, —C(O)NH(C$_{1-4}$ aliphatic), —C(O)N(C$_{1-4}$ aliphatic)$_2$, —O(halo-C$_{1-4}$ aliphatic), and halo (C$_{1-4}$ aliphatic), where each of the foregoing C$_{1-4}$ aliphatic groups of R* is unsubstituted; or two R* on the same nitrogen are taken together with the nitrogen to form a 5-8 membered heterocyclyl or heteroaryl ring having 1-3 heteroatoms independently selected from nitrogen, oxygen, and sulfur.

In some embodiments, optional substituents on the nitrogen of a non-aromatic heterocyclic ring include —R$^+$, —N(R$^+$)$_2$, —C(O)R$^+$, —C(O)OR$^+$, —C(O)C(O)R$^+$, —C(O)CH$_2$C(O)R$^+$, —S(O)$_2$R$^+$, —S(O)$_2$N(R$^+$)$_2$, —C(=S)N(R$^+$)$_2$, —C(=NH)—N(R$^+$)$_2$, or —NR$^+$S(O)$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, two independent occurrences of R$^+$, on the same substituent or different substituents, taken together with the atom(s) to which each R$^+$ group is bound, form a 5-8-membered heterocyclyl, aryl, or heteroaryl ring or a 3-8 membered cycloalkyl ring, wherein said heteroaryl or heterocyclyl ring has 1-3 heteroatoms independently selected from nitrogen, oxygen, or sulfur. Optional substituents on the aliphatic group or the phenyl ring of R$^+$ are selected from —NH$_2$, —NH(C$_{1-4}$ aliphatic), —N(C$_{1-4}$ aliphatic)$_2$, halogen, C$_{1-4}$ aliphatic, —OH, —O(C$_{1-4}$ aliphatic), —NO$_2$, —CN, —C(O)OH, —C(O)O(C$_{1-4}$ aliphatic), —O(halo(C$_{1-4}$ aliphatic)), or halo(C$_{1-4}$ aliphatic), wherein each of the foregoing C$_{1-4}$ aliphatic groups of R$^+$ is unsubstituted.

As detailed above, in some embodiments, two independent occurrences of R° (or R$^+$, or any other variable similarly defined herein), may be taken together with the atom(s) to which each variable is bound to form a 5-8-membered heterocyclyl, aryl, or heteroaryl ring or a 3-8-membered cycloalkyl ring. Exemplary rings that are formed when two independent occurrences of R° (or R$^+$, or any other variable similarly defined herein) are taken together with the atom(s) to which each variable is bound include, but are not limited to the following: a) two independent occurrences of R° (or R$^-$, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R$^+$, or any other variable similarly defined herein) that are bound to different atoms and are taken together with both of those atoms to form a ring, for example where a phenyl group is substituted with two occurrences of OR°

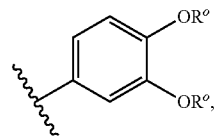

these two occurrences of R° are taken together with the oxygen atoms to which they are bound to form a fused 6-membered oxygen containing ring:

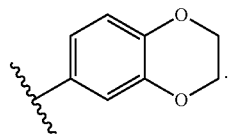 [SMILES: *c1ccc2c(c1)OCCO2]

It will be appreciated that a variety of other rings can be formed when two independent occurrences of R° (or R⁺, or any other variable similarly defined herein) are taken together with the atom(s) to which each variable is bound and that the examples detailed above are not intended to be limiting.

In some embodiments, a methylene unit of the alkyl or aliphatic chain is optionally replaced with another atom or group. Examples of such atoms or groups would include, but are not limited to, —NR°—, —O—, —S—, —C(O)O—, —OC(O)—, —C(O)CO—, —C(O)—, —C(O)NR°—, —C(=N—CN), —NR°CO—, —NR°C(O)O—, —S(O)₂NR°—, —NR°S(O)₂—, —NR°C(O)NR°—, —OC(O)NR°—, —NR°S(O)₂NR°—, —S(O)—, or —S(O)₂—, wherein R° is defined herein. Unless otherwise specified, the optional replacements form a chemically stable compound. Optional atom or group replacements can occur both within the chain and at either end of the chain; i.e. both at the point of attachment and/or also at the terminal end. Two optional replacements can also be adjacent to each other within a chain so long as it results in a chemically stable compound. Unless otherwise specified, if the replacement occurs at the terminal end, the replacement atom is bound to an H on the terminal end. For example, if one methylene unit of —CH₂CH₂CH₃ was optionally replaced with —O—, the resulting compound could be —OCH₂CH₃, —CH₂OCH₃, or —CH₂CH₂OH.

As described herein, a bond drawn from a substituent to the center of one ring within a multiple-ring system (as shown below) represents substitution of the substituent at any substitutable position in any of the rings within the multiple ring system. For example, Structure a represents possible substitution in any of the positions shown in Structure b.

Structure a

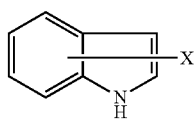

Structure b

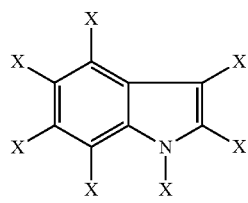

This also applies to multiple ring systems fused to optional ring systems (which would be represented by dotted lines). For example, in Structure c, X is an optional substituent both for ring A and ring B.

Structure c

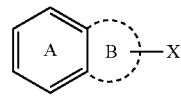

If, however, two rings in a multiple ring system each have different substituents drawn from the center of each ring, then, unless otherwise specified, each substituent only represents substitution on the ring to which it is attached. For example, in Structure d, Y is an optionally substituent for ring A only, and X is an optional substituent for ring B only.

Structure d

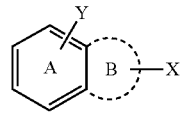

The term "protecting group," as used herein, represent those groups intended to protect a functional group, such as, for example, an alcohol, amine, carboxyl, carbonyl, etc., against undesirable reactions during synthetic procedures. Commonly used protecting groups are disclosed in Greene and Wuts, *Protective Groups In Organic Synthesis*, 3ʳᵈ Edition (John Wiley & Sons, New York, 1999), which is incorporated herein by reference. Examples of nitrogen protecting groups include acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl and chiral auxiliaries such as protected or unprotected D, L or D, L-amino acids such as alanine, leucine, phenylalanine and the like; sulfonyl groups such as benzenesulfonyl, p-toluenesulfonyl and the like; carbamate groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl and the like, arylalkyl groups such as benzyl, triphenylmethyl, benzyloxymethyl and the like and silyl groups such as trimethylsilyl and the like. Preferred N-protecting groups are formyl, acetyl, benzoyl, pivaloyl, t-butylacetyl, alanyl, phenylsulfonyl, benzyl, t-butyloxycarbonyl (Boc) and benzyloxycarbonyl (Cbz).

The term "prodrug," as used herein, represents a compound that is transformed in vivo into a compound of formula I or a compound listed in Table 1. Such a transformation can be affected, for example, by hydrolysis in blood or enzymatic transformation of the prodrug form to the parent form in blood or tissue. Prodrugs of the compounds of the invention may be, for example, esters. Esters that may be utilized as prodrugs in the present invention are phenyl esters, aliphatic ($C_1$-$C_{24}$) esters, acyloxymethyl esters, carbonates, carbamates, and amino acid esters. For example, a compound of the invention that contains an OH group may be acylated at this position in its prodrug form. Other prodrug forms include phosphates, such as, for example those phosphates resulting from the phosphonation of an OH group on the parent compound. A thorough discussion of prodrugs is provided in T. Higuchi and V. Stella, *Pro-drugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, and Judkins et al., *Synthetic Communications* 26(23):4351-4367, 1996, each of which is incorporated herein by reference.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools, probes in biological assays, or as PI3K inhibitors with improved therapeutic profile.

Description of Compounds of the Invention

In one aspect, the present invention features compounds having the formula:

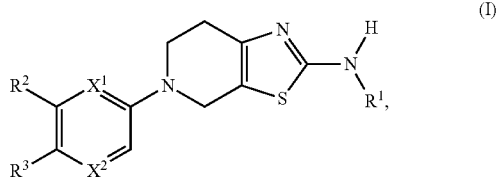

(I)

or a pharmaceutically acceptable salt thereof, wherein:
each of $X^1$ and $X^2$ is, independently, N or CH;
$R^1$ is —C(O)H, —C(O)$R^{1a}$, —C(O)N($R^{1a}$)($R^{1b}$), or a 5- or 6-membered heteroaryl ring having 1-3 heteroatoms selected from N, O, or S and optionally substituted with 1, 2 or 3 $J^{R2}$ groups;
$R^{1a}$ is $C_{1-6}$ aliphatic, $C_{3-6}$ cycloaliphatic, azetidinyl, pyrrolidinyl, or piperidinyl, wherein $R^{1a}$ is optionally substituted with 1, 2, 3, or 4, occurrences of $J^R$;
$R^{1b}$ is hydrogen, $C_{1-4}$ aliphatic, or $R^{1a}$ and $R^{1b}$, together with the nitrogen to which they are attached, form a 4-6 membered heterocyclic ring, wherein said heterocyclic ring of $R^{1a}$ and $R^{1b}$ optionally comprises one additional heteroatom selected from nitrogen and oxygen, and wherein said heterocyclic ring of $R^{1a}$ and $R^{1b}$ is optionally substituted with 1 or 2 $J^{R2}$ groups;
each $J^R$ is independently fluoro, oxo, —C(O)$J^{R1}$, —C(O)N($J^{R1}$)$_2$, —C(O)O($J^{R1}$), —N($J^{R1}$)C(O)$J^{R1}$, —O$J^{R1}$, —S$J^{R1}$, phenyl or a 5-6 membered heteroaryl or heterocyclyl having up to 2 atoms selected from nitrogen, oxygen, or sulfur, wherein said phenyl, heteroaryl, or heterocyclyl or $J^R$ is optionally substituted with 1 or 2 $J^{R2}$ groups;
each $J^{R1}$ is independently selected from hydrogen, $C_{1-4}$ aliphatic, $C_{3-6}$ cycloaliphatic, phenyl, benzyl, heterocyclyl, or heteroaryl, wherein said heterocyclyl of $J^{R1}$ is a 5- or 6-membered ring having 1 or 2 atoms selected from N, or O, said heteroaryl of $R^2$ is a 5- or 6-membered monocyclic ring or a 9- or 10-membered fused bicyclic ring system having 1, 2, or 3 atoms selected from N, O, or S, and each of said aliphatic, cycloaliphatic, phenyl, benzyl, heterocyclyl, or heteroaryl of $J^{R1}$ is optionally substituted with up to three $J^{R2}$ groups;
each $J^{R2}$ is selected from chloro, fluoro, oxo, $C_{1-2}$alkyl, $C_{1-2}$alkyl substituted with 1-3 fluorine atoms, $C_{3-6}$cycloalkyl, —OH, —O$C_{1-2}$alkyl, —O$C_{1-2}$alkyl substituted with 1-3 fluorine atoms, —C(O)$C_{1-2}$alkyl, or —S$C_{1-2}$alkyl;
$R^2$ is hydrogen, fluoro, chloro, $C_{1-6}$aliphatic, —O$C_{1-6}$aliphatic, $C_{3-6}$cycloaliphatic, —O$C_{3-6}$cycloaliphatic, cyano, —NH$_2$, —NH$C_{1-6}$aliphatic, —NH$C_{3-6}$cycloaliphatic, —NHS(O)$_2$$C_{1-6}$aliphatic, —NHS(O)$_2$$C_{3-6}$cycloaliphatic, —NHS(O)$_2$phenyl, —NHS(O)$_2$benzyl, —NHS(O)$_2$heteroaryl, —S(O)$_2$$C_{1-6}$aliphatic, —S(O)$_2$$C_{3-6}$cycloaliphatic, —S(O)$_2$phenyl, —S(O)$_2$benzyl, —S(O)$_2$heteroaryl, —S(O)$_2$NH$C_{1-6}$aliphatic, —S(O)$_2$NH$C_{3-6}$cycloaliphatic, —S(O)$_2$NHphenyl, —S(O)$_2$NHbenzyl, or —S(O)$_2$NHheteroaryl, wherein said heteroaryl of $R^2$ is a 5- or 6-membered ring having 1, 2, or 3 atoms selected from N, O, or S, and wherein said aliphatic, cycloaliphatic, phenyl, benzyl, or heteroaryl of $R^2$ is optionally substituted with 1, 2, or 3 $J^{R2}$ groups; and
$R^3$ is hydrogen, fluoro, chloro, $C_{1-3}$aliphatic, —O$C_{1-3}$aliphatic, NH$_2$, or NH$C_{1-3}$aliphatic, wherein said aliphatic of $R^3$ is optionally substituted with up to 3 occurrences of fluoro.

In one embodiment for compounds of formula I, each of $X^1$ and $X^2$ is N or $X^1$ is CH and $X^2$ is N; $R^1$ is —C(O)H, —C(O)$R^{1a}$, —C(O)N($R^{1a}$)($R^{1b}$), or a 6-membered heteroaryl ring having up to 2 nitrogen atoms and optionally substituted with 1, 2 or 3 $J^{R2}$ groups; $R^{1a}$ is $C_{1-4}$ aliphatic, azetidinyl, pyrrolidinyl, or piperidinyl, wherein $R^{1a}$ is optionally substituted with 1, 2, or 3 occurrences of $J^R$; $R^{1b}$ is hydrogen or $R^{1a}$ and $R^{1b}$, together with the nitrogen to which they are attached, form a 4-6 membered heterocyclic ring, wherein said heterocyclic ring of $R^{1a}$ and $R^{1b}$ optionally comprises one additional heteroatom selected from nitrogen and oxygen, and wherein said heterocyclic ring of $R^{1a}$ and $R^{1b}$ is optionally substituted with 1 or 2 $J^{R2}$ groups; each $J^R$ is independently fluoro, oxo, —C(O)$J^{R1}$, —C(O)N($J_{R1}$)$_2$, —C(O)O($J^{R1}$), —N($J^{R1}$)C(O)$J^{R1}$, —O$J^{R1}$, phenyl, or a 5-6 membered heteroaryl or heterocyclyl having up to 2 atoms selected from nitrogen, oxygen, or sulfur, wherein said phenyl, heteroaryl, or heterocyclyl or $J^R$ is optionally substituted with 1 or 2 $J^{R2}$ groups; each $J^{R1}$ is independently selected from hydrogen, $C_{1-4}$aliphatic, $C_{3-6}$cycloaliphatic, phenyl, benzyl, heterocyclyl, or heteroaryl, wherein said heterocyclyl of $J^{R1}$ is a 5- or 6-membered ring having 1 or 2 atoms selected from N, or O, said heteroaryl of $R^2$ is a 5- or 6-membered monocyclic ring having 1, 2, or 3 atoms selected from N, O, or S, and each of said aliphatic, cycloaliphatic, phenyl, benzyl, heterocyclyl, or heteroaryl of $J^{R1}$ is optionally substituted with up to three $J^{R2}$ groups; each $J^{R2}$ is selected from chloro, fluoro, oxo, $C_{1-2}$alkyl, $C_{1-2}$alkyl substituted with 1-3 fluorine atoms, $C_{3-6}$cycloalkyl, —OH, —O$C_{1-2}$alkyl, —O$C_{1-2}$alkyl substituted with 1-3 fluorine atoms, —C(O)$C_{1-2}$alkyl, or —S$C_{1-2}$alkyl; and each of $R^2$ and R[3] is, independently hydrogen, chloro, trifluoromethyl or —OCH$_3$, wherein at least one of R[2] and R[3] is not hydrogen.

In one embodiment, R[1] is —C(O)R$^{1a}$, —C(O)N(R$^{1a}$)(R$^{1b}$), or a 6-membered heteroaryl ring having up to 2 nitrogen atoms and optionally substituted with 1, 2 or 3 J$^{R2}$ groups;

In another embodiment, R[1] is —C(O)R$^{1a}$. In a further embodiment, —C(O)R$^{1a}$ is selected from

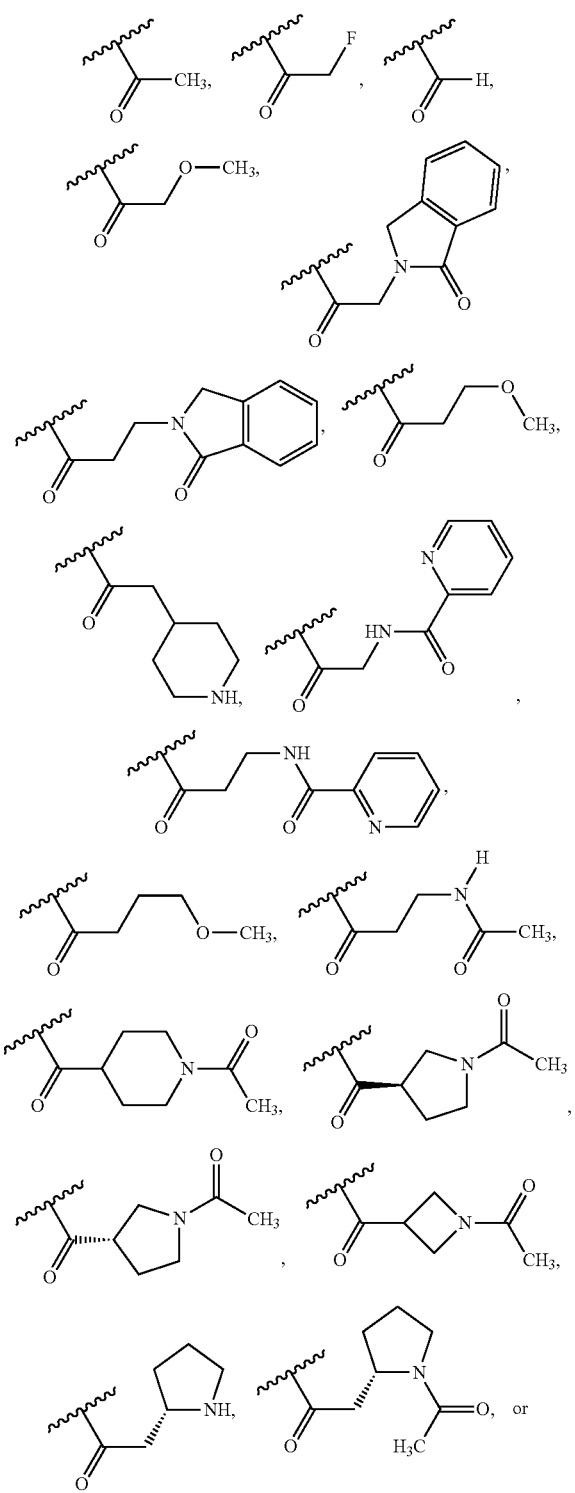

-continued

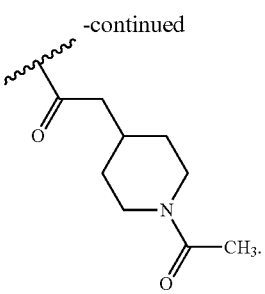

In one embodiment, R[1] is —C(O)N(R$^{1a}$)(R$^{1b}$). In a further embodiment, R[1] is —C(O)N(R$^{1a}$)(R$^{1b}$), wherein R$^{1b}$ is hydrogen and R$^{1a}$ is a C$_{1-4}$ aliphatic, optionally substituted with —OJ$^{R1}$ or a 5 membered heteroaryl having up to 2 atoms selected from nitrogen and optionally substituted with up to two J$^{R2}$ groups.

Alternatively, R$^{1a}$ and R$^{1b}$, together with the nitrogen to which they are attached, form a 4-6 membered heterocyclic ring, wherein said heterocyclic ring optionally comprises one additional heteroatom selected from nitrogen and oxygen, and wherein said heterocyclic ring is optionally substituted with 1 or 2 J$^{R2}$ groups.

In yet another embodiment, —C(O)N(R$^{1a}$)(R$^{1b}$) is selected from

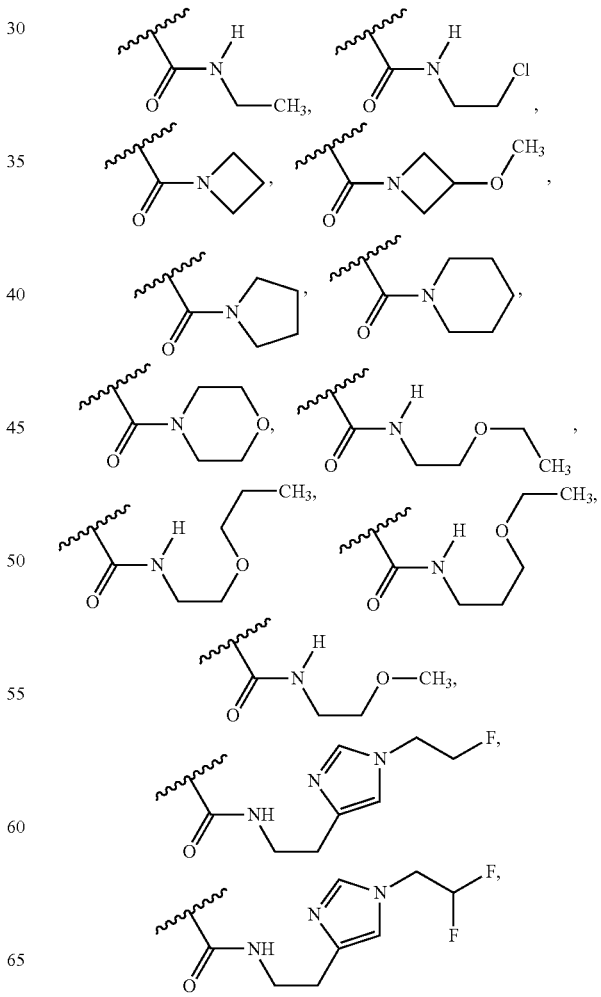

-continued

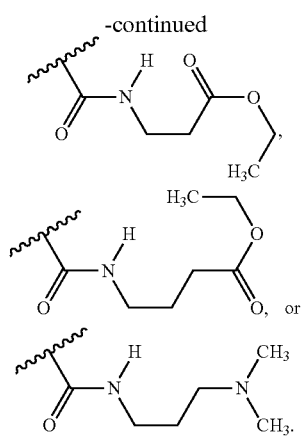

In another embodiment, R¹ is a 5- or 6-membered heteroaryl ring having 1-3 heteroatoms selected from N, O, or S and optionally substituted with 1, 2, or 3 $J^{R2}$ groups. In a further embodiment, R¹ is an optionally substituted pyridine, pyrimidine, pyrazine, or pyridazine ring.

In a further embodiment, R¹ is selected from

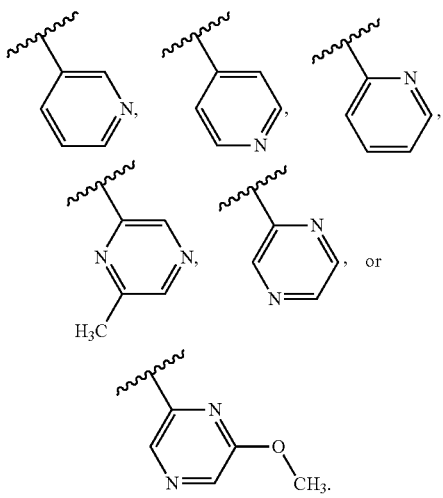

In one embodiment of a compound of formula I, or a pharmaceutically acceptable salt thereof, each of $X^1$ and $X^2$ is N. In another embodiment, $X^1$ is CH and $X^2$ is N. In yet another embodiment, each of $X^1$ and $X^2$ is CH.

In another embodiment,

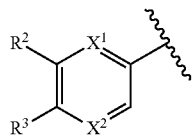

is selected from:

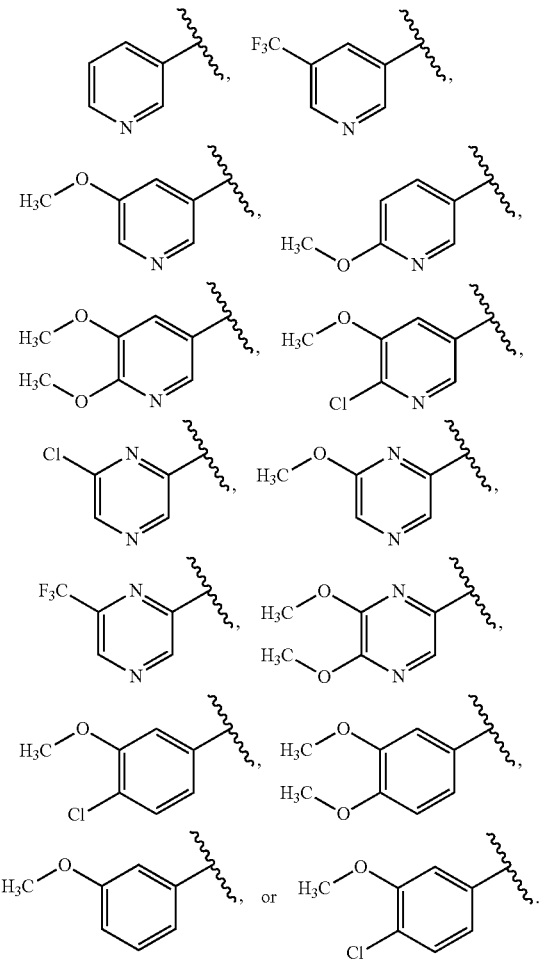

In yet another embodiment, the invention features a compound selected from the group of compounds listed in Table 1.

TABLE 1

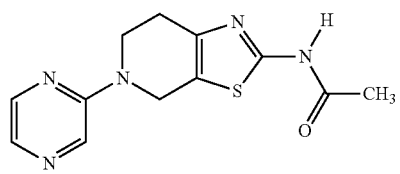 [SMILES: CC(=O)Nc1nc2c(s1)CN(c1cnccn1)CC2]

1

TABLE 1-continued
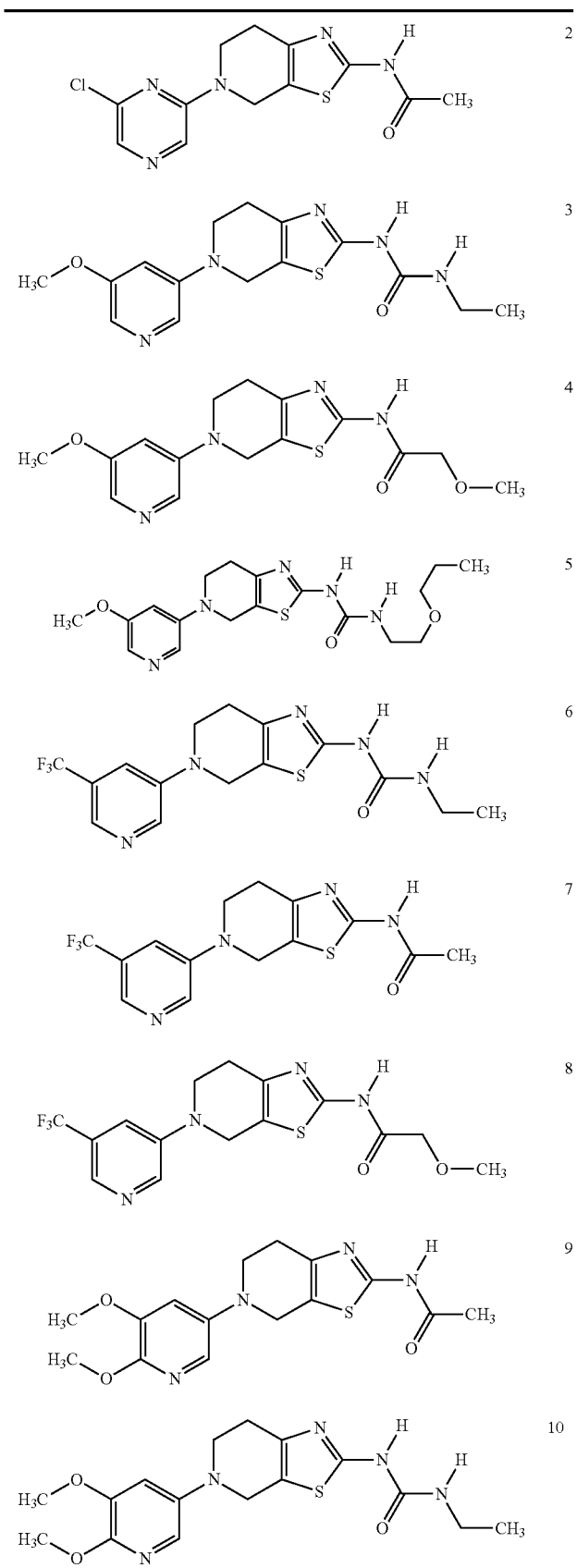

TABLE 1-continued
| | |
|---|---|
| 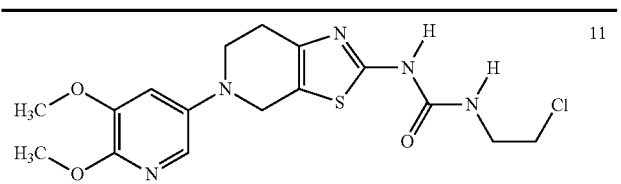 | 11 |
| 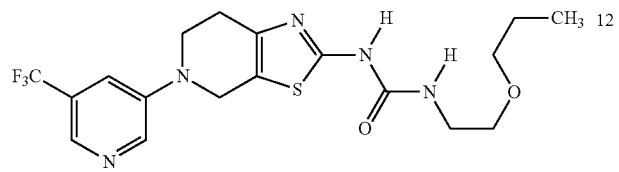 | 12 |
| 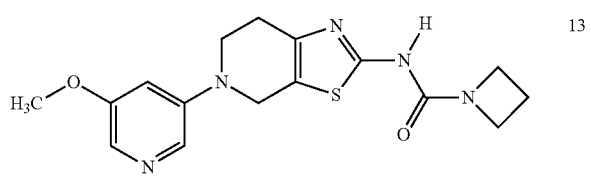 | 13 |
| 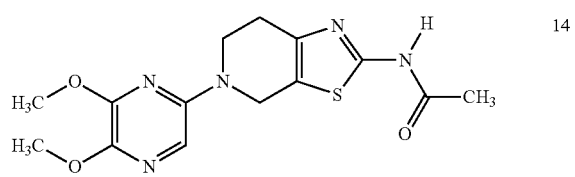 | 14 |
| 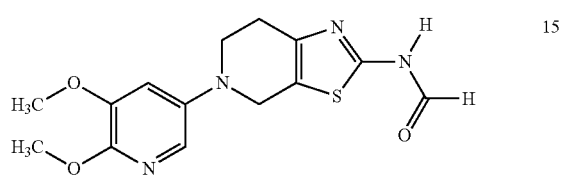 | 15 |
| 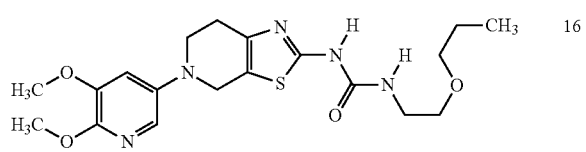 | 16 |
| 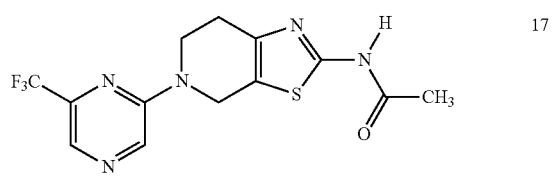 | 17 |
| 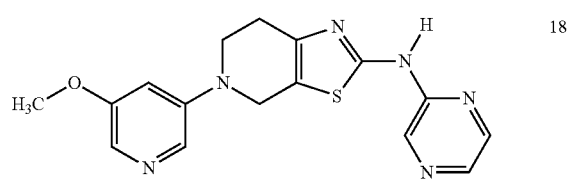 | 18 |
| 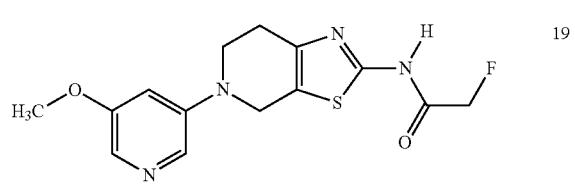 | 19 |

TABLE 1-continued
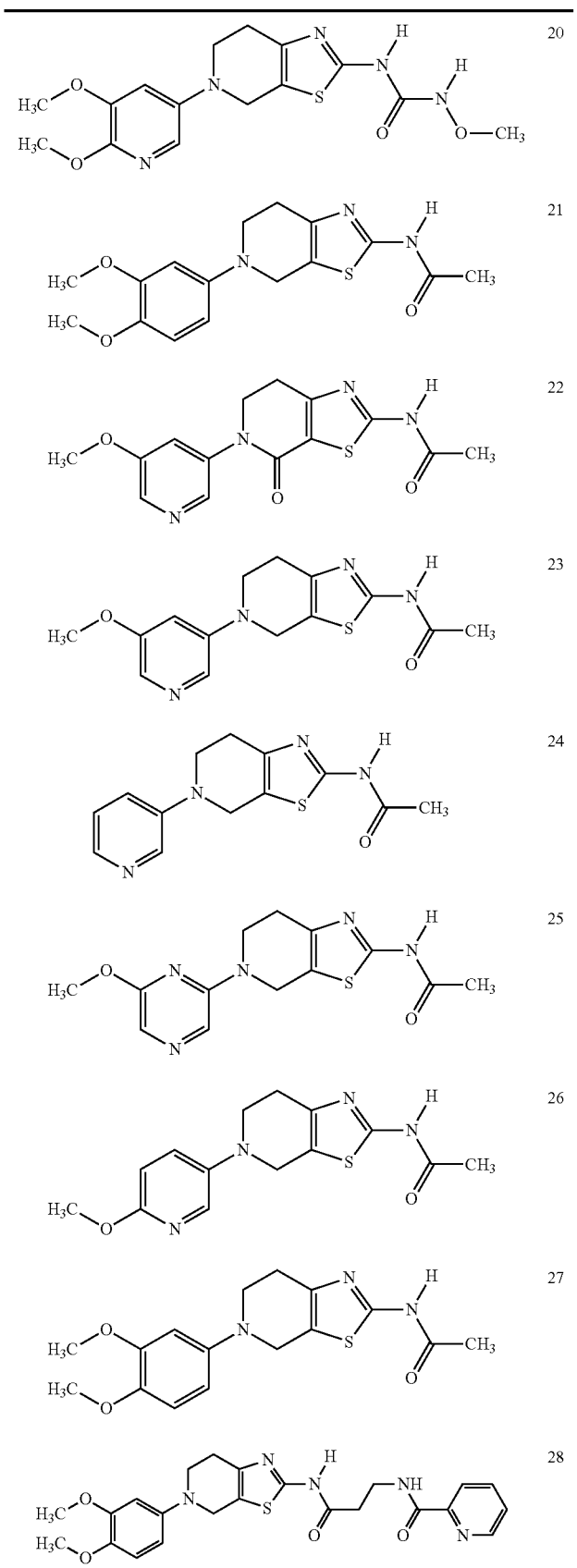

TABLE 1-continued

| | |
|---|---|
| (structure) | 29 |
| (structure) | 30 |
| (structure) | 31 |
| (structure) | 32 |
| (structure) | 33 |
| (structure) | 34 |
| (structure) | 35 |
| (structure) | 36 |
| (structure) | 37 |
| (structure) | 38 |

TABLE 1-continued
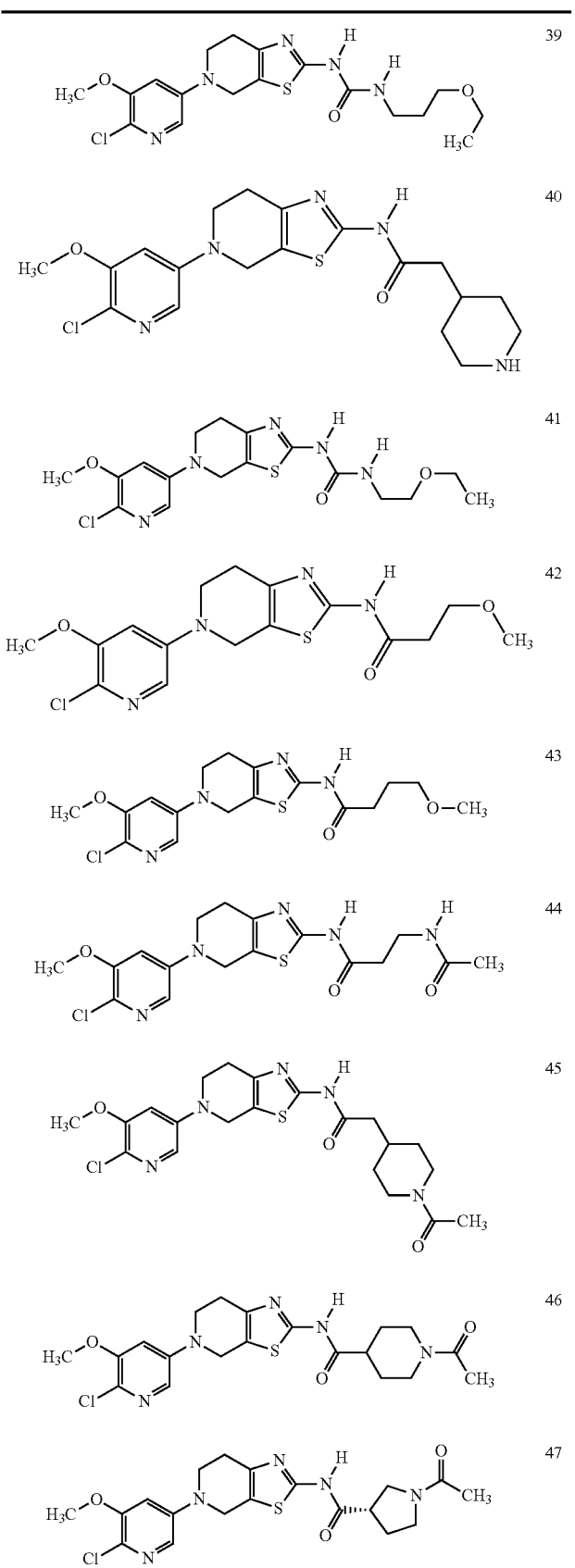

TABLE 1-continued

TABLE 1-continued

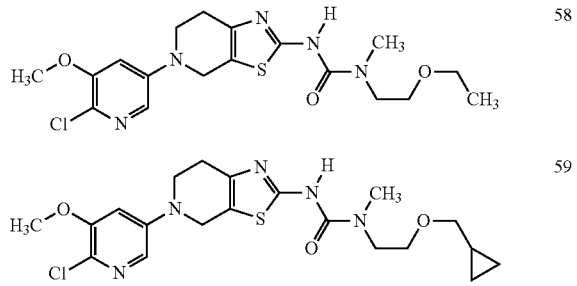

The invention also features a pharmaceutical composition comprising a compound of the invention and a pharmaceutically acceptable carrier, adjuvant, or vehicle.

Compositions, Formulations, and Administration of Compounds of the Invention

In another embodiment, the invention provides a pharmaceutical composition comprising a compound of any of the formulae or classes described herein. In a further embodiment, the invention provides a pharmaceutical composition comprising a compound of Table 1. In a further embodiment, the composition additionally comprises an additional therapeutic agent.

According to another embodiment, the invention provides a composition comprising a compound of this invention or a pharmaceutically acceptable derivative thereof and a pharmaceutically acceptable carrier, adjuvant, or vehicle. In one embodiment, the amount of compound in a composition of this invention is such that is effective to measurably inhibit a PI3K, particularly PI3Kγ, in a biological sample or in a patient.

In one embodiment, the composition of this invention is formulated for administration to a patient in need of such composition. In a further embodiment, the composition of this invention is formulated for oral administration to a patient. The term "patient," as used herein, means an animal, preferably a mammal, and most preferably a human.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof. As used herein, the term "inhibitory active metabolite or residue thereof" means that a metabolite or residue thereof is also an inhibitor of PI3K.

As used herein, the term "pharmaceutically acceptable salt" refers to those salts which are, within the scope of sound medical judgment, suitable for use in contact with the tissues of humans and lower animals without undue toxicity, irritation, allergic response and the like.

Pharmaceutically acceptable salts are well known in the art. For example, S. M. Berge et al., describe pharmaceutically acceptable salts in detail in *J. Pharmaceutical Sciences*, 66:1-19, 1977, which is incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: *The Science and Practice of Pharmacy*, 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional, epidural, intraspinal, and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, dissolving or suspending the compound in an oil vehicle accomplishes delayed absorption of a parenterally administered compound form. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated." Examples of additional therapeutic agents are provided infra.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Uses of the Compounds and Compositions of the Invention

In one embodiment, the invention comprises a method of treating or lessening the severity of a PI3K-mediated condition or disease in a patient. The term "PI3K-mediated disease", as used herein means any disease or other deleterious condition in which a PI3K isoform is known to play a role. In one embodiment, the PI3K isoform is PI3Kγ. In a further embodiment, the invention comprises a method of treating a PI3K-mediated disease. Such conditions include, without limitation, autoimmune diseases, inflammatory diseases, thrombolytic diseases, cancer, cardiovascular diseases, diabetes, allergic diseases, asthma and respiratory diseases. Specific examples of diseases to be treated by the compounds or compositions of the invention include atherosclerosis, inflammatory bowel disease (IBD), macular degeneration, pancreatitis, hypertension, In another embodiment, the invention provides a method of treating or lessening the severity of a PI3K-mediated condition or disease in the brain or spinal cord of a patient, the method comprising administering to said patient a compound or composition of the invention. Diseases of the brain or spinal chord include, multiple sclerosis, Alzheimer's disease, Parkinson's disease, Huntington's disease, stroke, traumatic head injury, spinal chord injury, HIV encephalopathy, ischemic brain, and epilepsy.

In another embodiment, the invention provides a method of treating or lessening the severity of an autoimmune disease or disorder by administering to said patient a compound or composition of the invention. Autoimmune diseases or disorders include, without limitation, rheumatoid arthritis, systemic lupus erythematosus (SLE), multiple sclerosis, glomerulonephritis, scleroderma, chronic thyroiditis, Graves' disease, autoimmune gastritis, type I diabetes, autoimmune hemolytic anemia, autoimmune neutropenia, thrombocytopenia, atopic dermatitis, myasthenia gravis, inflammatory bowel disease, ulcerative colitis, Crohn's disease, psoriasis, Sjogren's syndrome and graft vs. host disease. In one particular embodiment, the autoimmune disease or disorder is rheumatoid arthritis, SLE or multiple sclerosis. In another particular embodiment, the disease is multiple sclerosis.

In another embodiment, the invention provides a method of treating or lessening the severity of an inflammatory disease by administering to said patient a compound or composition of the invention. Inflammatory diseases include, without limitation, chronic obstructive pulmonary disease (COPD), bronchitis, emphysema, farmer's lung and related diseases, eosinophilia, lung fibrosis, osteoarthritis, ankylosing spondylitis, sepsis, septic shock, inflammatory myopathies, meningitis, encephalitis, lacrimal parotid gland syndrome, acute respiratory distress syndrome and pancreatitis. In one embodiment, the inflammatory disease is acute respiratory distress syndrome or lacrimal parotid gland syndrome.

In another embodiment, the invention provides a method of treating or lessening the severity of allergic diseases or asthma. Examples of allergic diseases include, without limitation, perennial and seasonal allergic rhinitis, type I hypersensitivity reactions, atopic dermatitis, contact dermatitis, or eczema.

Compounds or compositions of the invention may be administered with one or more additional therapeutic agents, wherein the additional therapeutic agent is appropriate for the disease being treated and the additional therapeutic agent is administered together with a compound or composition of the invention as a single dosage form or separately from the compound or composition as part of a multiple dosage form. The additional therapeutic agent may be administered at the same time as a compound of the invention or at a different time. In the latter case, administration may be staggered by, for example, 6 hours, 12 hours, 1 day, 2 days, 3 days, 1 week, 2 weeks, 3 weeks, 1 month, or 2 months.

The invention provides a method of inhibiting PI3K kinase activity in a biological sample that includes contacting the biological sample with a compound or composition of the invention. The term "biological sample," as used herein, means a sample outside a living organism and includes, without limitation, cell cultures or extracts thereof; biopsied material obtained from a mammal or extracts thereof; and blood, saliva, urine, feces, semen, tears, or other body fluids or extracts thereof. Inhibition of kinase activity, particularly PI3K kinase activity, in a biological sample is useful for a variety of purposes known to one of skill in the art. Examples of such purposes include, but are not limited to, biological specimen storage and biological assays. In one embodiment, the method of inhibiting PI3K kinase activity in a biological sample is limited to non-therapeutic methods.

Preparation of Compounds of the Invention

As used herein, all abbreviations, symbols and conventions are consistent with those used in the contemporary scientific literature. See, e.g., Janet S. Dodd, ed., *The ACS Style Guide: A Manual for Authors and Editors,* 2nd Ed., Washington, D.C.: American Chemical Society, 1997. The following definitions describe terms and abbreviations used herein:

ATP adenosine triphosphate
Boc t-butoxylcarbonyl
Brine a saturated NaCl solution in water
DCM dichloromethane
DIEA diisopropylethylamine
DMF dimethylformamide
DMSO methylsulfoxide
DTT dithiothreitol
ESMS electrospray mass spectrometry
$Et_2O$ ethyl ether
EtOAc ethyl acetate
EtOH ethyl alcohol
HEPES 4-(2-hydroxyethyl)-1-piperazineethanesulfonic acid
HPLC high performance liquid chromatography LC-MS liquid chromatography-mass spectrometry
Me methyl
MeOH methanol
NBS N-bromosuccinimide
NMP N-methylpyrrolidone
Ph phenyl
RT or rt room temperature
tBu tertiary butyl
tBuOH tent-butanol
TCA trichloroacetic acid
THF tetrahydrofuran
TEA triethylamine
TFA trifluoacetic acid
XPhos 2-dicyclohexylphosphino-2',4',6'-triisopropylbiphenyl Unless otherwise indicated, purifications by reversed-phase HPLC were conducted on a Waters 20×100 mm YMC-Pack Pro C18 column using a linear water/acetonitrile (0.1% TFA, 0.2% formic acid, or 5 mmol ammonium formate) gradient at a flow rate of 28 mL/minute.

General Synthetic Procedures

In general, the compounds of this invention may be prepared by methods described herein or by other methods known to those skilled in the art.

Example 1

General Preparation of the Compounds of Formula I

The preparation of compounds of formula I, wherein $R^1$ is —C(O)$R^{1a}$, —C(O)N($R^{1a}$)$_2$, or a heteroaryl ring is shown in Scheme 1. Accordingly, a compound of formula A1, where $R^2$, $R^3$, and $X^1$, and $X^2$ are as defined for a compound of formula I, is reacted with a protected piperidin-4-one under basic conditions using a Buchwald catalyst such as 2-dicyclohexylphosphino-2',4',6'-triisopropylbiphenyl (XPhos) to produce a compound of formula A2 [see (a) Mauger, C. C.; Mignani, G. A. *Aldrichimica Acta* 2006, 39, 17; (b) Schlummer, B.; Scholz, U. *Adv. Synth. Catal.* 2004, 346, 1599; or Billingsley, K.; Buchwald, S. L. *J. Am. Chem. Soc.* 2007, 129, 3358]. After removal of the keto protecting group, the resulting ketone is reacted with sulfur and cyanamide under basic conditions at elevated temperature to produce a compound of formula A3. The primary amine of a compound of formula A3 can be used to form ureas such as compounds of formulae A4 and A5, wherein $R^{1a}$ and $R^{1b}$ are as defined for a compound of formula I. The primary amine of a compound of formula A3 can also be reacted with esters or carboxylic acids (through their activated esters) by methods known to those skilled in the art to form compounds having the formula A6. The primary amine of a compound of formula A3 can also be reacted with a haloheteroaromatic ring in the presence of cesium carbonate to form compounds having the formula A7.

In general, the compounds of this invention may be prepared by methods described herein or known to those skilled in the art for the preparation of analogous compounds. In order that the invention described herein may be more fully understood, the following examples are set forth. It should be understood that these examples are for illustrative purposes only and are not to be construed as limiting this invention in any manner.

Scheme 1

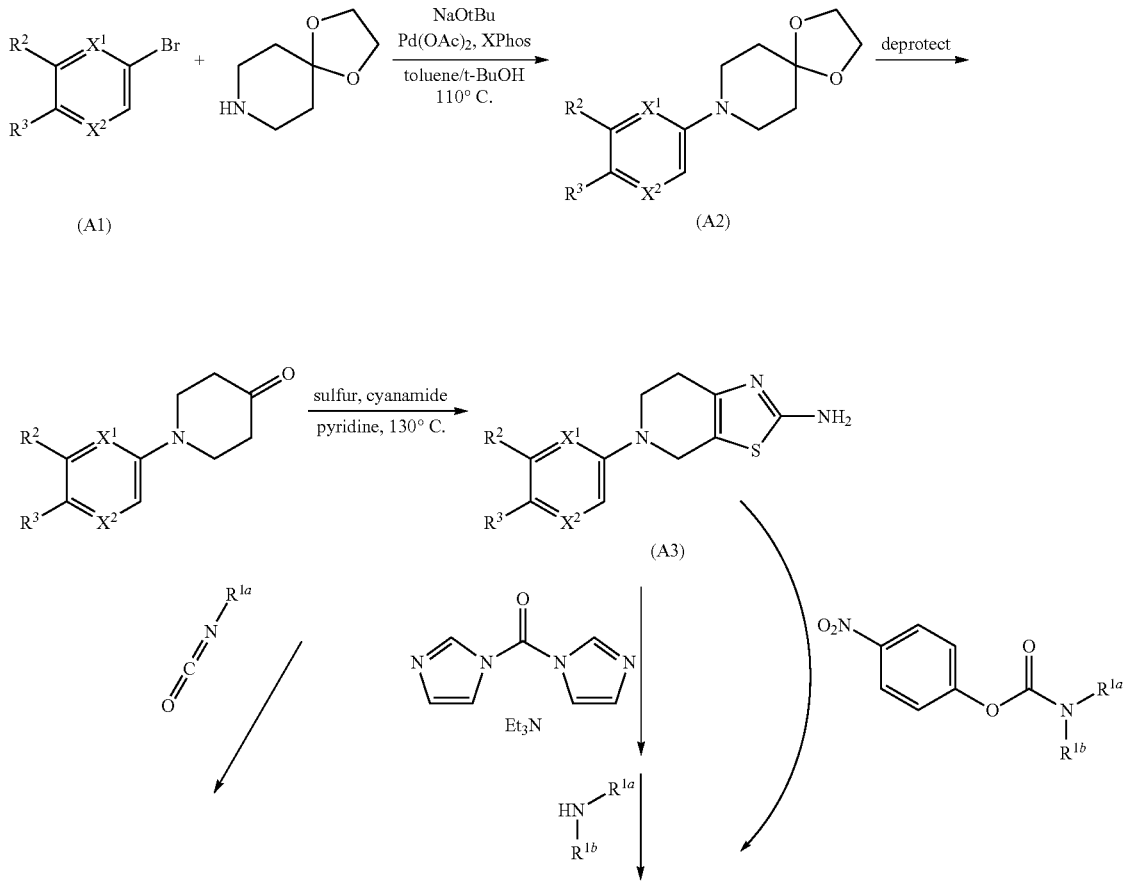

-continued

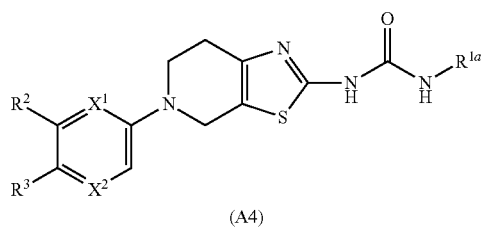

(A4)

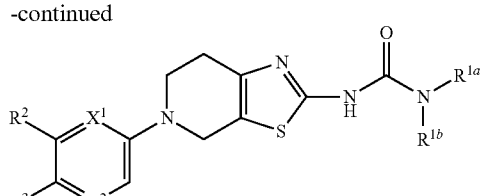

(A5)

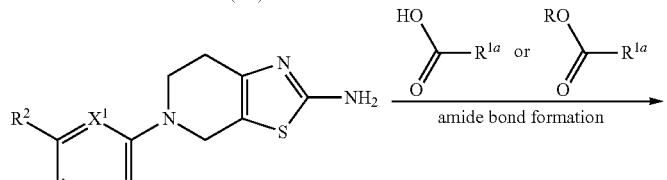

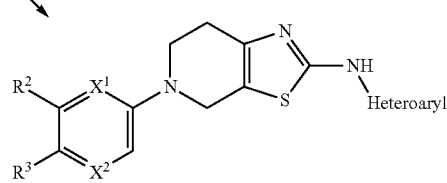

(A6)

Heteroary-Hal
Cs₂CO₃
NMP, 110° C.

(A7)

Example 2

Preparation of 3-ethoxy-2-methoxy-5-bromopyridine (Compound 1004)

As shown in step 2-i of Scheme 2, to 4.0 g (0.1 mol, 60% in mineral oil) NaH in a 100 mL DMF suspension was added 10 mL of an absolute ethyl alcohol (4.6 g, 0.1 mol)/DMF solution at RT. After the evolution of hydrogen gas, the reaction mixture was stirred at RT for 30 minutes and the resulting ethoxide solution transferred to a solution of 3,5-dibromopyridine (11.84 g, 0.05 mol, obtained from Aldrich Chemical Co.) in 100 mL DMF at 60° C. The reaction was stirred at 60° C. for 4 hours and the mixture was allowed to come to RT. Brine and ethyl acetate were added and the organics were partitioned, dried over MgSO₄, filtered, and the volatiles removed under reduced pressure. The resulting crude material was purified by silica chromatography, with the desired product eluting with 20% ethyl acetate/hexanes. 3-Bromo-5-ethoxypyridine (Compound 1001, 4.25 g) was obtained as the pure product (42% yield): ¹H NMR (CDCl₃) δ 8.3 (dd, 2H), 7.4 (d, 1H), 4.12 (q, 2H), 1.45 (t, 3H). 3-Benzyloxy-5-bromopyridine was prepared by an analogous procedure: ¹H NMR (CDCl₃) δ 8.33 (d, 2H), 7.5-7.35 (m, 6H), 5.15 (s, 2H).

Alternatively, as shown in step 2-ii of Scheme 2, 3-bromo-5-hydroxypyridine (100 mg, 0.57 mmol, obtained from Aldrich Chemical Co.) was diluted with DMF (3 mL). Potassium carbonate (158.8 mg, 1.15 mmol) was added, followed by the addition of bromoethane (62.6 mg, 42.6 μL, 0.57 mmol). The mixture was warmed to 60° C. and stirred overnight. After cooling, the mixture was dissolved in ethyl acetate and washed with 2 M NaOH, followed by water. The organics were dried over sodium sulfate, filtered, and the volatiles removed under reduced pressure. The resulting crude 3-bromo-5-ethoxypyridine (Compound 1001) was used without further purification. The following compounds were made by an analogous procedure: 3-bromo-5-propoxypyridine, ESMS (M+H) 218.19/216.19; 3-bromo-5-butylpyridine, ESMS (M+H) 230.22/232.22; 3-bromo-5-(cyclohexylmethoxy)pyridine, ESMS (M+H) 270.2/272.22; 3-(2-fluoroexthoxy)-5-bromopyridine, ESMS (M+H) 220.14/222.14; 3-(2,2-difluoroexthoxy)-5-bromopyridine; and 3-(2-ethylbutoxy)-5-bromopyridine, ESMS (M+H) 258.33/256.33.

As shown in step 2-iii of Scheme 2, 3-chloroperoxybenzoic acid (9.426 g, 42.06 mmol) was added to 3-bromo-5-methoxypyridine (4.25 g, 21 mmol) in 200 mL of DCM at RT. The reaction was stirred overnight and the mixture was washed with 200 mL of 2 N NaOH and 2×200 mL brine. The organic phase was dried over MgSO₄, filtered and the volatiles removed under reduced pressure to provide 3-bromo-5-ethoxypyridine, 1-oxide (Compound 1002, 4.4 g): ¹H NMR (CDCl₃): δ 8.05 (s, 1H), 7.9 (s, 1H), 7.0 (s, 1H), 4.12 (q, 2H), 1.45 (t, 3H).

As shown in step 2-iv of Scheme 2, phosphorous oxychloride (48.02 g, 403.6 mmol) was added to 3-bromo-5-ethoxypyridine, 1-oxide (4.4 g, 20.18 mmol) in 700 mL of DCM at RT. The reaction mixture was stirred at RT overnight. After the addition of brine, the organics were partitioned, dried over MgSO₄, filtered, and the filtrate concentrated under reduced pressure. The product was purified by filtering the concentrate through a pad of silica gel and eluting the pad with ethyl acetate. The volatiles were removed under reduced pressure to provide 5-bromo-2-chloro-3-ethoxypyridine (Compound 1003, 4.3 g, 85.6%): ¹H NMR (CDCl₃) δ 8.1 (s, 1H), 7.32 (s, 1H), 4.15 (q, 2H), 1.6 (t, 3H).

As shown in step 2-v of Scheme 2, 40.51 mL of a 25% MeONa/MeOH solution was added to 5-bromo-2-chloro-3-ethoxypyridine (4.3 g, 17.27 mmol). The reaction mixture was refluxed for 2 hours. After cooling, ethyl acetate and brine were added to the mixture. The organic phase was dried with MgSO$_4$, filtered, and evaporated under reduced pressure. After purification via silica gel chromatography, 5-bromo-3-ethoxy-2-methoxypyridine (Compound 1004, 2.1 g, 50% yield) was obtained: $^1$H NMR (CDCl$_3$) δ 7.8 (s, 1H), 7.15 (s, 1H), 4.1 (q, 2H), 4.0 (s, 3H), 1.5 (t, 3H). The following compounds were synthesized by an analogous procedure: 5-Bromo-3-isopropoxy-2-methoxypyridine: $^1$H NMR (CDCl$_3$) δ 7.7 (s, 1H), 7.1 (s, 1H), 4.55-4.5 (m, 1H), 3.9 (s, 3H), 1.3 (d, 6H); 5-bromo-2-ethoxy-3-methoxypyridine: ESMS (M+H) 232, 234; 5-bromo-3-methoxy-2-propoxypyridine: ESMS (M+H) 246, 248; 5-bromo-2-isopropoxy-3-methoxypyridine: ESMS (M+H) 246, 248; 5-bromo-2-(2,2-difluoroethoxy)-3-methoxypyridine: ESMS (M+H) 268, 270; 5-bromo-2,3-diethoxypyridine: ESMS (M+H) 246, 248; 5-bromo-2-(2,2-difluoroethoxy)-3-ethoxypyridine: ESMS (M+H) 282, 284; 5-bromo-3-ethoxy-2-propoxypyridine: ESMS (M+H) 260, 262; 5-bromo-3-ethoxy-2-isopropoxypyridine: ESMS (M+H) 260, 262; 5-bromo-3-(2-fluoroethoxy)-2-methoxypyridine: ESMS (M+H) 250, 252; 5-bromo-2-methoxy-3-propoxypyridine: ESMS (M+H) 246, 248; 5-bromo-2-methoxy-3-(2-methoxyethoxy)pyridine: ESMS (M+H) 262, 264; 5-bromo-3-(2,2-difluoroethoxy)-2-methoxypyridine: $^1$H NMR (CDCl$_3$) δ 7.9 (d, 1H), 7.2 (d, 1H), 6.1 (tt, 1H), 4.4 (q, 2H), 4.2 (td, 2H), 1.4 (t, 3H); 5-bromo-2-ethoxy-3-isopropoxypyridine: $^1$H NMR (CDCl$_3$) δ 7.7 (d, 1H), 7.1 (d, 1H), 4.4 (m, 1H), 4.3 (q, 2H), 1.3 (m, 9H); 5-bromo-3-butoxy-2-methoxypyridine: ESMS (M+H) 260, 262; 5-bromo-2-methoxy-3-(2,2,2-trifluoroethoxy)pyridine: ESMS (M+H) 286, 288; and 5-bromo-2-ethoxy-3-(2,2,2-trifluoroethoxy)pyridine: ESMS (M+H) 300, 302.

Also prepared by a procedure analogous to that of step 2-v were 5-methoxy-3-bromopyridine, 2,3-dimethoxy-5-bromopyridine, 2,3-diethoxy-5-bromopyridine, 2-methoxy-3-propoxy-5-bromopyridine, and 2-methoxy-3-(2-methoxyethoxy)-5-bromo)pyridine.

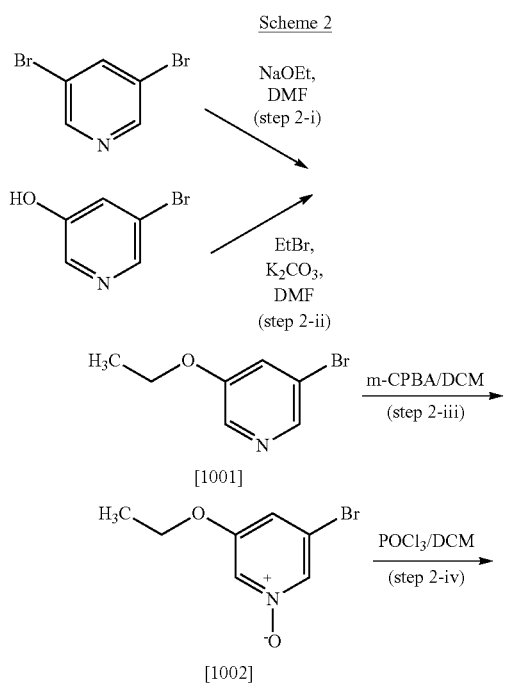

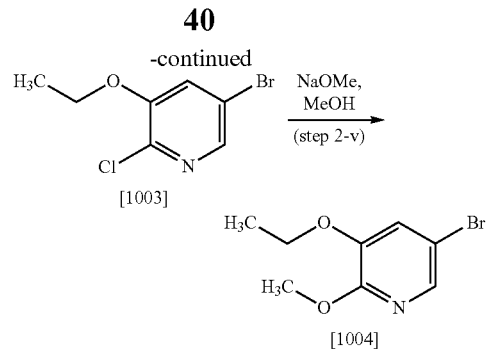

Example 3

Preparation of 5-bromo-3-(difluoromethoxy)-2-methoxypyridine (Compound 1010)

As shown in step 3-i of Scheme 3, 2-chloro-3-hydroxypyridine (Compound 1005, 2.0 g, 15.4 mmol, obtained from Aldrich Chemical Co.) was dissolved in 40 mL of DMF and 5.0 mL of water along with sodium chlorodifluoroacetate (4.71 g, 30.9 mmol, obtained from Lancaster Synthesis, Inc.) and anhydrous potassium carbonate (2.56 g; 18.5 mmol). The reaction mixture was heated in an oil bath at 100° C. for 2 hours. Another equivalent of sodium chlorodifluoroacetate and 1.2 equiv. of potassium carbonate were added and heating continued for an additional 2.0 hours. After this time, the reaction was cooled and the volatiles removed under reduced pressure. The residue was partitioned between brine and ethyl acetate and the organics washed once more with brine, dried over Na$_2$SO$_4$, filtered, and the volatiles removed under reduced pressure. The product was purified by silica gel chromatography, eluting with a hexanes/DCM to DCM gradient, to produce 2-chloro-3-(difluoromethoxy)pyridine as a white solid (Compound 1006, 2.0 g, 72% yield): ESMS (M+H) 180; $^1$H NMR (CDCl$_3$) δ 8.05 (m, 1H), 7.45 (m, 1H), 6.90 (m, 1H), 6.60 (t, 1H; J=75 Hz), 4.01 (s, 3H).

As shown in step 3-ii of Scheme 3, an excess of sodium metal was dissolved into 20 mL anhydrous methanol and 2-chloro-3-(difluoromethoxy)pyridine (2.0 g, 11.1 mmol) in anhydrous methanol was added. The reaction mixture was stirred in a sealed vessel at 100° C. for 6 hours. The volatiles were removed under reduced pressure and the residue was partitioned between EtOAc and brine. The brine was extracted with EtOAc and the combined organics were dried over Na$_2$SO$_4$, filtered, and the volatiles removed under reduced pressure. The product was purified by silica gel chromatography (DCM) to yield 3-(difluoromethoxy)-2-methoxypyridine as a colorless oil (Compound 1007, 1.1 g, 56% yield: ESMS (M+H) 176.

As shown in step 3-iii of Scheme 3, 3-(difluoromethoxy)-2-methoxypyridine (270 mg, 1.54 mmol) was dissolved in 5 mL of DCM and BBr$_3$ (540 μL; 1275 mg; 4.10 mmol) in heptane was added. The reaction mixture was stirred for 10 minutes at RT under an atmosphere of nitrogen, brought to reflux, and then stirred an additional 4 hours. The mixture was cooled and water was added to quench the reaction. The pH was adjusted to 7-8 with sodium bicarbonate, the organics partitioned, and the aqueous layer saturated with NaCl and extracted twice more with DCM. The combined organics were dried over Na$_2$SO$_4$, filtered, and the volatiles removed under reduced pressure. The product was purified by silica gel chromatography (DCM to 5% MeOH/DCM gradient) to yield 3-(difluoromethoxy)pyridin-2-ol as a white solid (Compound 1008, 986 mg, 97% yield): ESMS (M+H) 162.

As shown in step 3-iv of Scheme 3, 3-(difluoromethoxy)pyridin-2-ol (986 mg; 6.12 mmol) was dissolved in 25 mL of glacial acetic acid and sodium acetate (79 mg; 9.6 mmol) was added. The mixture was cooled in an ice bath and bromine (780 μL; 1.63 g; 10.22 mmol) in 10 mL of glacial acetic acid was added over 10 minutes. The reaction was stirred for 30 minutes at 10-15° C. The volatiles were removed under reduced pressure and the residue was partitioned between brine/saturated sodium carbonate solution and ethyl acetate. After the evolution of gas ceased, the organic and aqueous layers were separated and the aqueous solution extracted three additional times with EtOAc. The combined organics were dried over $Na_2SO_4$, filtered, and the volatiles removed under reduced pressure. The residue was purified twice by silica gel chromatography (first a DCM to 10% MeOH/DCM gradient then 1:1 EtOAc/hexanes) to provide 5-bromo-3-(difluoromethoxy)pyridin-2-ol as a light yellow powder (Compound 1009, 810 mg, 55% yield): ESMS (M+H) 241.9/243.9; $^1$H NMR ($CDCl_3$) δ 13.2 (br m, 1H), 7.44 (d, 1H, J=2.1 Hz), 7.18 (d, 1H, J=2.1 Hz), 6.92 (t, 1H, J=75 Hz).

As shown in step 3-v of Scheme 3, 5-bromo-3-(difluoromethoxy)pyridin-2-ol (300 mg; 1.25 mmol) was dissolved in 5 mL of chloroform. Silver carbonate (690 mg; 2.5 mmol) and methyl iodide (780 μL; 1.77 g; 12.5 mmol) were added and the mixture stirred at RT overnight. The reaction mixture was filtered through diatomaceous earth, which was washed with additional $CHCl_3$. The filtrates were concentrated under reduced pressure to yield an oil which was purified by silica gel chromatography to yield 5-bromo-3-(difluoromethoxy)-2-methoxypyridine as a white solid (Compound 1010, 250 mg, 78% yield): ESMS (M+H) 254/256; $^1$H NMR ($CDCl_3$) δ 8.08 (d, 1H, J=2.1 Hz), 7.56 (d, 1H, J=2.1 Hz), 6.60 (t, 1H, J=75 Hz), 3.98 (s, 3H).

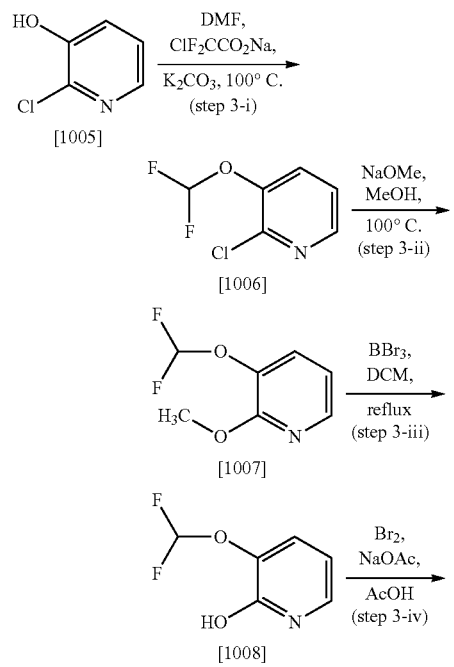

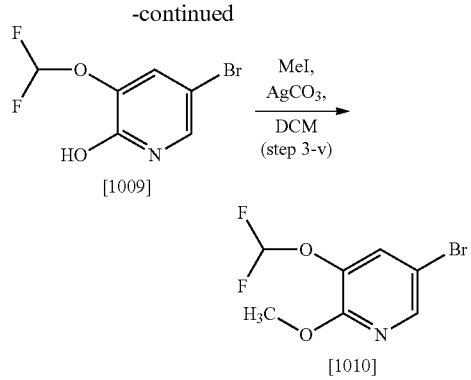

Example 4

Preparation of 2.5-dibromo-3-ethoxypyridine (Compound 1015)

As shown in step 4-i of Scheme 4, 1,1'-carbonyldiimidazole (57.4 g, 354.2 mmol) was added to a solution of 2-amino-3-hydroxypyridine (26.0 g, 236.1 mmol, obtained from Aldrich Chemical Co.) in THF (400 mL). The resulting reaction mixture was stirred at 70° C. for 14 h. The reaction mixture was cooled to RT and concentrated under reduced pressure. The residue was dissolved in DCM (500 mL) and washed with 2 N NaOH (3×100 mL). The combined aqueous layers were cooled to 0° C. and acidified to a pH of 6 with 6 N HCl. The precipitate that was formed was collected in a fitted funnel, washed with cold water (100 mL), and dried under vacuum to afford oxazolo[4,5-b]pyridin-2(3H)-one (Compound 1011, 26.0 g, 81% yield): ESMS (M+H) 137; $^1$H NMR (DMSO-$d_6$) δ 12.4 (br, 1H), 8.0 (d, 1H), 7.6 (d, 1H), 7.1 (dd, 1H).

As shown in step 4-ii of Scheme 4, bromine (10.8 mL, 210.1 mmol) was added dropwise over 20 min to a stirring solution of Compound 1011 (26.0 g, 191 mmol) in DMF (200 mL). The reaction mixture was stirred at RT for 14 h. The mixture was poured onto crushed ice and the precipitate that formed was collected in a fitted funnel. The solid was washed with water (200 mL) and dried under vacuum to afford 6-bromooxazolo[4,5-b]pyridine-2(3H)-one (Compound 1012, 37.0 g, 91% yield) as a light yellow solid: ESMS (M+H) 215, 217; $^1$H NMR (DMSO-$d_6$) δ 12.6 (br, 1H), 8.2 (s, 1H), 8.0 (s, 1H).

As shown in step 4-iii of Scheme 20, Compound 1012 (34 g, 158.1 mmol) was diluted with 10% NaOH(aq) (500 mL), and the resulting mixture was stirred at 100° C. for 6 h. The reaction was cooled to 5° C., and 6 N HCl was added until a precipitate formed (ca. pH 10). The solid was collected in a fritted funnel, washed with water (200 mL), and dried under vacuum to afford 2-amino-5-bromo-3-hydroxypyridine (Compound 1013, 24.0 g, 80% yield) as a tan solid: ESMS (M+H) 189, 191; $^1$H NMR (DMSO-$d_6$) δ 7.5 (s, 1H), 6.9 (s, 1H), 5.7 (br, 2H).

As shown in step 4-iv of Scheme 20, Compound 1013 (19.0 g, 100.5 mmol) was dissolved in DCM (90 mL), and iodoethane (9.0 mL, 110.6 mmol), Adogen® 464 (methyltrialkyl ($C_8$-$C_{10}$)ammonium chloride, 0.6 g), and 40% NaOH(aq) (90 mL) were added. The reaction was stirred at RT for 21 h. The DCM layer was separated, and the aqueous layer was diluted with water (100 mL) and extracted with DCM (2×100 mL). The combined organic extracts were dried over $Na_2SO_4$ and concentrated under reduced pressure. The crude product was purified on a silica plug eluting with 40% ethyl acetate/hexanes to afford 2-amino-5-bromo-3-ethoxypyridine (Compound 1014, 10.0 g, 46% yield) as a white solid: ESMS (M+H) 217, 219. $^1$H NMR (DMSO-$d_6$) δ 7.6 (s, 1H), 7.1 (s, 1H), 5.8 (br, 2H), 4.0 (q, 2H), 1.3 (t, 3H).

As shown in step 4-v of Scheme 4, Compound 1014 (10 g, 46.1 mmol) was diluted with 48% hydrobromic acid (90 mL, 530 mmol) and cooled to 0° C. Bromine (8.0 mL, 148 mmol) was added dropwise, followed by the addition of a 40 wt % solution of sodium nitrite (40.0 mL, 231 mmol). The dark black heterogeneous solution was stirred at 0° C. for 1 h. The reaction mixture was adjusted to a pH of 13 using 50% NaOH (aq), and the solids that formed were collected in a fritted funnel and washed with water (300 mL). The crude solid product was dissolved in DCM (500 mL), washed with 1 M $Na_2S_2O_3$ (50 mL) and brine (50 mL), dried over $Na_2SO_4$, and concentrated under reduced pressure to afford 2,5-dibromo-3-ethoxypyridine (Compound 1015, 10.0 g, 73% yield) as a light yellow solid: ESMS (M+H) 280, 282, 284; $^1$H NMR (DMSO-$d_6$) δ 8.1 (s, 1H), 7.8 (s, 1H), 4.2 (q, 2H), 1.4 (t, 3H).

under reduced pressure. The resulting aqueous solution was extracted with DCM and ether, followed by drying the combined extracts over MgSO4. After filtration, removal of the volatiles under reduced pressure provided 5-bromo-2-ethoxy-3-methoxypyridine (Compound 1016), 0.72 g, 69% yield): ESMS (M+H) 232.32/234.23. As shown in step 5-ii of Scheme 5, Compound 1017 (ESMS (M+H) 218.32/220.23) was prepared in the same manner as Compound 1016, using sodium methoxide in methanol instead of sodium ethoxide in ethanol.

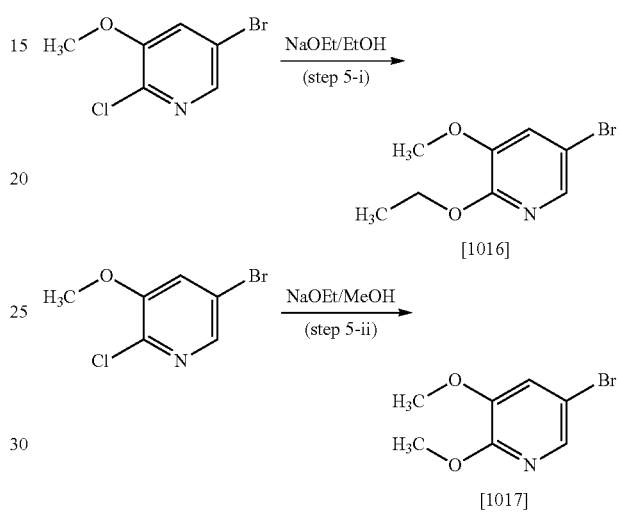

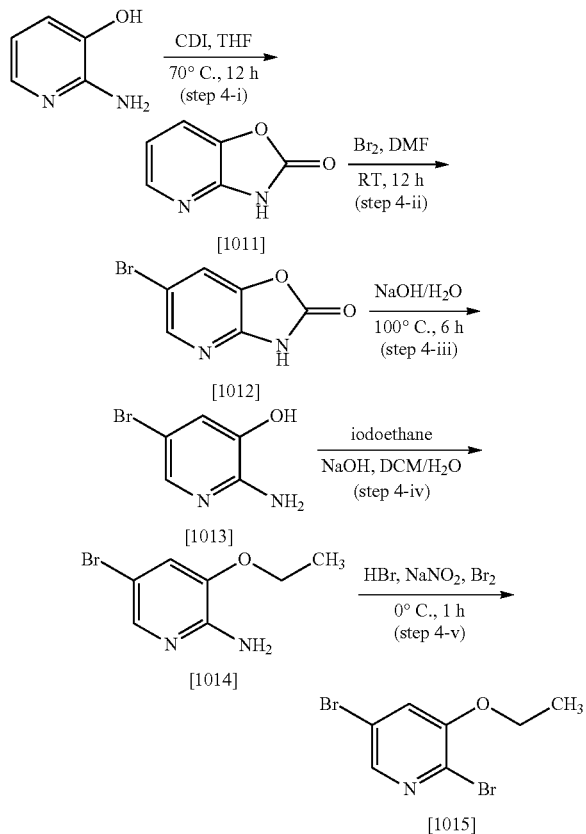

Example 5

Preparation of 5-bromo-2-ethoxy-3-methoxypyridine (Compound 1016) and 5-bromo-2,3-dimethoxypyridine (Compound 1017)

As shown in step 5-i of Scheme 5, 5-bromo-2-chloro-3-methoxypyridine (1.0 g, 4.5 mmol, prepared in the same manner as Compound 1003 in Example 2 starting with 3-bromo-5-methoxypyridine) was treated with a sodium ethoxide/ethanol solution (5.05 mL, 21% w/v, 13.5 mmol) and the reaction mixture microwave irradiated at 100° C. for 20 minutes. Water was added and the ethanol evaporated

Example 6

Preparation of 5-bromo-3-methoxy-2-methylpyridine (Compound 1021), 5-bromo-2-cyclopropyl-3-methoxypyridine (Compound 1022), and 5-bromo-2-isopropoxy-3-methoxypyridine (Compound 1023)

As shown in step 6-i of Scheme 6, calcium chloride (4.0 g, 35.7 mmol) was added to a stirring solution of 3-methoxy-2-nitropyridine (5.0 g, 32.5 mmol, obtained from AK Scientific, Inc.) in methanol (100 mL) and water (25 mL). The reaction mixture was warmed to 75° C. and iron powder (4.6 g, 81.1 mmol) was added carefully over 10 min. The resulting reaction mixture was stirred at 75° C. for another 2 h. The reaction mixture was cooled to RT and filtered through a pad of diatomaceous earth. The pad was rinsed with ethanol (400 mL) and the filtrate was evaporated under reduced pressure. The residue was suspended in ethyl acetate/water (1/1, 200 mL), the organic layer was separated, and the aqueous layer was extracted with ethyl acetate (3×100 mL). The combined organic extracts were washed with brine (60 mL), dried over $Na_2SO_4$, and concentrated under reduced pressure to afford 2-amino-3-methoxypyridine (Compound 1018, 3.6 g, 89% yield): ESMS (M+H) 125; $^1$H NMR (DMSO-$d_6$) δ 7.5 (d, 1H), 7.0 (d, 1H), 6.5 (dd, 1H), 5.6 (br, 2H), 3.75 (s, 3H).

As shown in step 6-ii of Scheme 6, bromine (6.3 mL, 120.8 mmol) was added dropwise to a stirring solution of Compound 1018 (15 g, 120.8 mmol) in acetic acid (150 mL) at RT. The resulting reaction mixture was stirred at RT for 16 h. The reaction mixture was concentrated under reduced pressure, and the acetic acid was removed by azeotropic distillation with toluene (2×100 mL) under reduced pressure. The residue was cooled to 0° C. and neutralized with saturated sodium bicarbonate solution until a pH of 7 was achieved. The aqueous mixture was extracted with ethyl acetate (4×500 mL). The combined organic extracts were washed with brine (60 mL), dried over $Na_2SO_4$, and concentrated under reduced pressure. The residue was purified on a plug of silica, eluting with 50% ethyl acetate/hexanes to afford 2-amino-5-bromo-3-methoxypyridine (Compound 1019, 20.0 g, 81% yield): ESMS (M+H) 203, 205; $^1H$ NMR (DMSO-$d_6$) δ 7.6 (s, 1H), 7.2 (s, 1H), 6.0 (br, 2H), 3.8 (s, 3H).

As shown in step 6-iii of Scheme 6, Compound 1019 (109.0 g, 536.8 mmol) was diluted with 48% hydrobromic acid (1.0 L, 6.2 mol), and the reaction mixture was cooled to 0° C. Bromine (89.0 mL, 1.72 mol) was added dropwise, followed by the addition of a 40 wt % solution of sodium nitrite (463.1 mL, 2.68 mol) over 40 min. The dark black heterogeneous mixture was stirred at 0° C. for 1 hour. The reaction mixture was adjusted to a pH of 13 with 50% NaOH (aq) and warmed to RT over 1 hour. Solids formed, which were collected on a fritted funnel and washed with water (3×1.0 L). The crude solid product was dissolved in DCM (2.0 L), washed with 1 M $Na_2S_2O_3$ (2×500 mL) and brine (500 mL), dried over $Na_2SO_4$, and concentrated under reduced pressure to afford 2,5-dibromo-3-methoxypyridine (Compound 1020, 126.0 g, 88% yield) as a light yellow solid: ESMS (M+H) 266, 268, 270; $^1H$ NMR (DMSO-$d_6$) δ 8.1 (s, 1H), 7.8 (s, 1H), 3.9 (s, 3H).

As shown in step 6-iv of Scheme 6, Compound 1020 (5 g, 18.73 mmol) was dissolved in dry THF (94 mL) and $Pd(PPh_3)_4$ (2.16 g, 1.873 mmol) was added. The reaction mixture was cooled in an ice bath, and methylmagnesium bromide in 3/1 THF/toluene (17.4 mL, 1.4 M, 24.35 mmol) was slowly added. The ice bath was removed, and the reaction was heated to reflux. The reaction was stirred at reflux for 1 h and 3 mL of the methylmagnesium bromide solution were added. The reaction was stirred at reflux for another 20 min and 2 mL of the methylmagnesium bromide solution were added. The reaction was stirred at reflux for 1 h and cooled to RT. Ethyl ether and 1 N HCl were added, and the organic layer was separated and washed with 1 N HCl. The aqueous extracts were washed with ethyl ether three times. The aqueous layer was made basic with 2 N NaOH and extracted with ethyl acetate three times. The ethyl acetate extracts were combined and dried over $Na_2SO_4$, then concentrated under reduced pressure. The residue was purified via silica gel chromatography (0-25% ethyl acetate/hexanes) to afford 5-bromo-3-methoxy-2-methylpyridine (Compound 1021, 2.7 g, 71% yield): ESMS (M+H) 202, 204. 5-Bromo-2-ethyl-3-methoxypyridine was made by an analogous procedure: ESMS (M+H) 216, 218; 1H NMR (CDCl$_3$) δ 8.2 (d, 1H), 7.2 (d, 1H), 3.8 (s, 3H), 2.8 (q, 2H), 1.2 (t, 3H).

As shown in step 6-v of Scheme 6, Compound 1020 (3.6 g, 13.5 mmol), potassium cyclopropyl-trifluoro-boron (2.5 g, 16.9 mmol), and potassium phosphate (8.6 g, 40.5 mmol) were taken up in about 80 mL of a toluene/water mixture. The reaction mixture was flushed with nitrogen gas for 10 minutes and $Pd(PPh_3)_4$ (1.4 g, (1.21 mmol) was added. The reaction mixture was refluxed for 18 hours, resulting in a mixture of products by HPLC analysis. The reaction was cooled, diluted with EtOAc and saturated NaCl. The organics were separated, dried (MgSO$_4$), and concentrated under reduced pressure to provide a solid, which was purified by medium pressure silica gel chromatography (0-8% EtOAc/hexanes gradient) to give 5-bromo-2-cyclopropyl-3-methoxypyridine (Compound 1022, 0.54 g, 70% pure): ESMS (M+H) 227.9/229.9. This compound was used as is in subsequent reactions.

As shown in step 6-vi of Scheme 6, 2-propanol (287 µL, 3.75 mmol) in 1 mL DMF was added to a suspension of sodium hydride (187 mg/60% in mineral oil, 4.682 mmol) in 4 mL DMF at RT. The mixture was stirred for 30 minutes, then added to a stirring solution of 2,5-dibromo-3-methoxypyridine (500 mg, 1.873 mmol, Compound 1020) in 4 mL DMF at 60° C. The reaction was heated at 60° C. for 2 hours. After cooling to RT, water and ethyl acetate were added and the layers separated. The aqueous layer was extracted with ethyl acetate and the organics were combined, dried over MgSO$_4$, filtered, and concentrated under reduced pressure. The residue was adsorbed onto silica gel, which was eluted with ethyl acetate/hexanes (0-40%) to provide 5-bromo-2-isopropoxy-3-methoxypyridine (Compound 1023, 0.16 g, 35% yield): $^1H$ NMR (CDCl$_3$) δ 7.77 (d, J=2.1 Hz, 1H), 7.13 (d, J=2.0 Hz, 1H), 5.35 (septet, J=6.2 Hz, 1H), 3.87 (s, 3H), 1.40 (d, J=6.2 Hz, 6H). 5-Bromo-3-methoxy-2-propoxypyridine and 5-bromo-2-(2,2-difluoroethoxy)-3-methoxypyridine were prepared by an analogous procedure.

Scheme 6

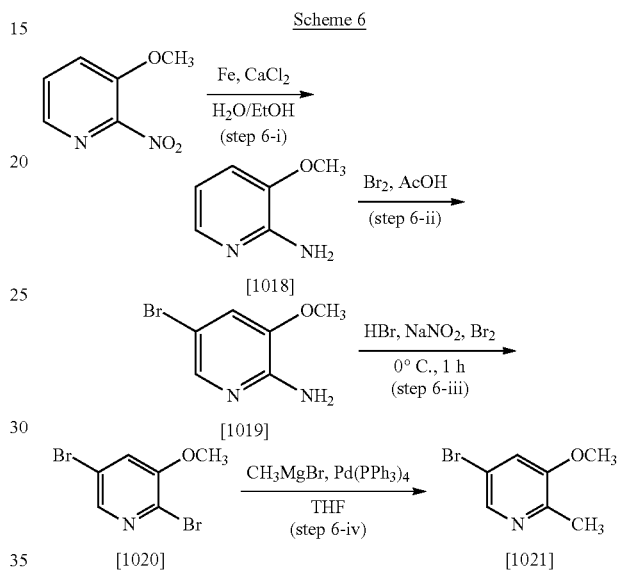

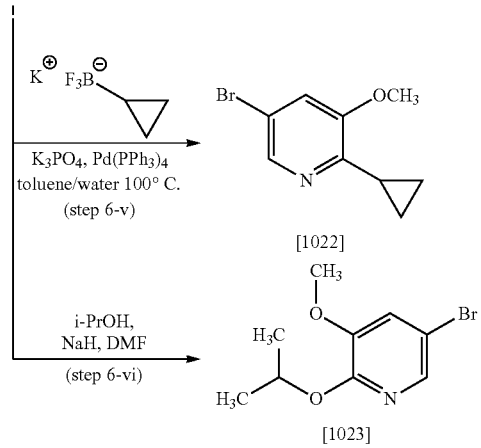

Example 7

Preparation of 1-ethyl-3-(5-(5-methoxypyridin-3-yl)-4,5,6,7-tetrahydrothiazolo[5,4-c]pyridin-2-yl)urea (Compound 3) and 1-(4,5,6,7-tetrahydro-5-(5-methoxypyridin-3-yl)thiazolo[5,4-c]pyridin-2-yl)-3-(2-propoxyethyl)urea (Compound 5)

As shown in step 7-i of Scheme 7, a 250 mL flame dried round bottom flask was charged with 1,4-dioxa-8-azaspiro

[4.5]decane (3.525 g, 3.119 mL, 24.62 mmol), 3-bromo-5-methoxypyridine (4.63 g, 24.62 mmol) in 120 mL of toluene:tBuOH (5:1). Palladium (II) acetate (276.4 mg, 1.231 mmol) and XPhos (586.8 mg, 1.231 mmol) were then added and the reaction mixture was purged with nitrogen for 90 min. Sodium t-butoxide (2.602 g, 27.08 mmol) was added and the reaction mixture was refluxed for 8 hours, followed by cooling to room temperature. The crude dark reaction mixture was filtered off, the filtrate was concentrated under reduced pressure and directly purified by medium pressure flash chromatography (50 to 80% EtOAc/hexanes) to yield 8-(5-methoxy-pyridin-3-yl)-1,4-dioxa-8-azaspiro[4.5]decane (Compound 1024, 4.3 g, 70% yield): ESMS (M+H) 251.12; $^1$H NMR (300 MHz, CDCl$_3$) δ 7.97 (d, J=2.4 Hz, 1H), 7.79 (d, J=2.4 Hz, 1H), 7.26 (s, 1H), 6.71 (m, 1H), 3.99 (s, 4H), 3.84 (s, 3H), 3.36 (m, 4H) and 1.83 (t, J=5.8 Hz, 4H) ppm.

As shown in step 7-ii of Scheme 7, to a solution of Compound 1024 (4.3 g, 17.18 mmol) in dioxane (10 mL) was added 6N aq. HCl (10 mL) and the reaction solution was stirred for 4 hours at room temperature. The solution was slowly brought to a pH of 9 by addition of solid Na$_2$CO$_3$. Water (50 mL) was added to the reaction mixture, followed by extraction with EtOAc (2×50 mL). The combined organic fractions were washed with brine (20 mL), dried over MgSO$_4$, and concentrated under reduced pressure to give 1-(5-methoxypyridin-3-yl)piperidin-4-one (Compound 1025, 3.09 g 87% yield) as a thick pale yellow oil, which was used without further purification: ESMS (M+H) 207.08; $^1$H NMR (300 MHz, CDCl$_3$) δ 8.00 (d, J=2.4 Hz, 1H), 7.84 (d, J=2.3 Hz, 1H), 6.73 (t, J=2.4 Hz, 1H), 3.85 (s, 3H), 3.64-3.60 (m, 3H) and 2.56 (t, J=6.1 Hz, 3H) ppm.

As shown in step 7-iii of Scheme 7, a 50 mL round bottom flask was charged with Compound 1025 (206 mg, 1 mmol), sulfur (64.1 mg, 2.0 mmol), fresh cyanamide (84.0 mg, 2.9 mmol) in pyridine (3 mL). The reaction solution was stirred at reflux for 100 minutes at 130° C. The solution turned from light yellow to red to dark red. The reaction mixture was cooled to room temperature and the solvent was removed under reduced pressure. The residue was triturated with MeOH, the resulting mixture filtered, and the filtrate concentrated under reduced pressure. The residue was purified by medium-pressure silica gel chromatography (0 to 5% MeOH in DCM) to yield 5-(5-methoxypyridin-3-yl)-4,5,6,7-tetrahydrothiazolo[5,4-c]pyridin-2-amine as an amber solid (Compound 1026, 62 mg, 24% yield): $^1$H NMR (CD$_3$OD with 2 drops of DMSO-d$_6$) δ 7.90 (d, J=2.4 Hz, 1H), 7.68 (d, J=2.1 Hz, 1H), 6.97 (t, J=2.4 Hz, 1H), 4.29 (m, 2H), 3.85 (s, 3H), 3.69 (t, J=5.7 Hz, H), 2.65 (m, 2H) ppm.

As shown in step 7-iv of Scheme 7, to a solution of Compound 1026 (50 mg, 0.19 mmol) in DMF (2 mL) was added ethyl isocyanate (135.5 mg, 149.7 µL, 1.91 mmol). The solution was heated in a microwave for 5 min at 120° C. The crude solution was concentrated and purified by medium-pressure silica gel chromatography (eluting sequentially with DCM, 0-3% MeOH in DCM, then isocratic 3% MeOH/DCM) to give 1-ethyl-3-(5-(5-methoxypyridin-3-yl)-4,5,6,7-tetrahydrothiazolo[5,4-c]pyridin-2-yl)urea (Compound 3, 43.4 mg) as a yellow solid, which was subsequently salted as its monomesylate salt: ESMS (M+H) 334.05; 332.08; $^1$H NMR (CD$_3$OD, 300 MHz) δ 8.13 (d, J=2.1 Hz, 1H), 7.88 (d, J=2.1 Hz, 1H), 7.61 (d, J=2.1 Hz, 1H), 4.59 (t, J=1.5 Hz, 2H), 4.012 (s, 3H), 3.89 (t, J=5.7 Hz, 2H), 3.28 (q, J=7.2 Hz, 2H), 2.84 (m, 2H), 2.71 (s, 3H, MsOH), 1.17 (t, J=7.2 Hz, 3H) ppm.

As shown in step 7-v of Scheme 7, 5-(5-methoxypyridin-3-yl)-4,5,6,7-tetrahydrothiazolo[5,4-c]pyridin-2-amine (Compound 1026, 100 mg, 0.46 mmol) was stirred with 1,1'-carbonyldiimidazole (74.2 mg, 0.4574 mmol) and triethylamine (48.2 mg, 66.4 µL, 0.48 mmol) in chloroform (approximately 10 mL resulting in a partial suspension) and heated at 50° C. for 7 hours. A gradual formation of yellow precipitate (Compound 1027) was noted over time and the reaction mixture was cooled to RT and used as is without processing.

As shown in step 7-vi of Scheme 7, to the above reaction mixture in chloroform (~10 mL) was added DMF (2 mL) and 2-n-propoxyethylamine (118 mg, 1.14 mmol), DIEA (0.132 mL, 0.76 mmol) and heated at 50° C. for 2 hours, then stirred at RT overnight. The reaction mixture was quenched with water and concentrated under reduced pressure. The residue was purified by medium pressure silica gel chromatography (0 to 10% MeOH in DCM) to give 1-(4,5,6,7-tetrahydro-5-(5-methoxypyridin-3-yl)thiazolo[5,4-c]pyridin-2-yl)-3-(2-propoxyethyl)urea (Compound 5) as light yellow solid, which was converted at the bis-HCl with 4N HCl in dioxane: $^1$H NMR (CDCl$_3$) δ 8.04 (d, J=2.4 Hz, 1H), 7.84 (d, J=2.4 Hz, 1H), 6.75 (t, J=2.4 Hz, 1H), 4.37 (s, 2H), 3.86 (s, 3H), 3.69 (t, J=6 Hz, 2H), 3.54 (m, 4H), 3.43 (t, J=6.6 Hz, 2H), 2.85 (t, J=5.7 Hz, 2H) 1.60 (m, 2H), 0.93 (t, J=7.5 Hz, 3H) ppm.

Using the appropriate bromopyridine corresponding to 3-bromo-5-methoxy-pyridine and either the appropriate isocyante in a step corresponding to step 7-iv or amine in the step corresponding to step 7-vi, the following compounds were similarly prepared: Compounds 3, 6, 10 to 13, 16, 20, 34 to 39, 41, 50-52, and 55-59.

Scheme 7

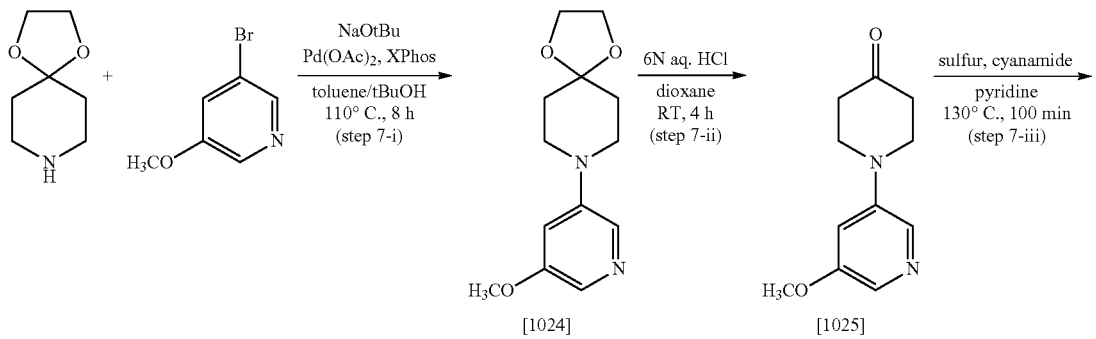

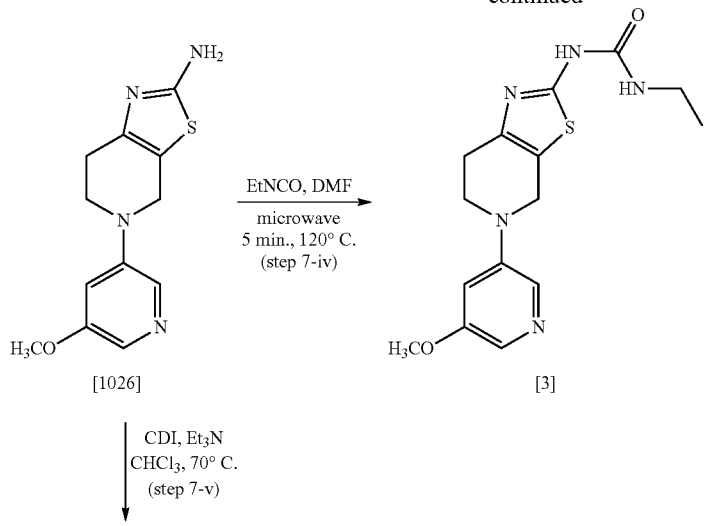

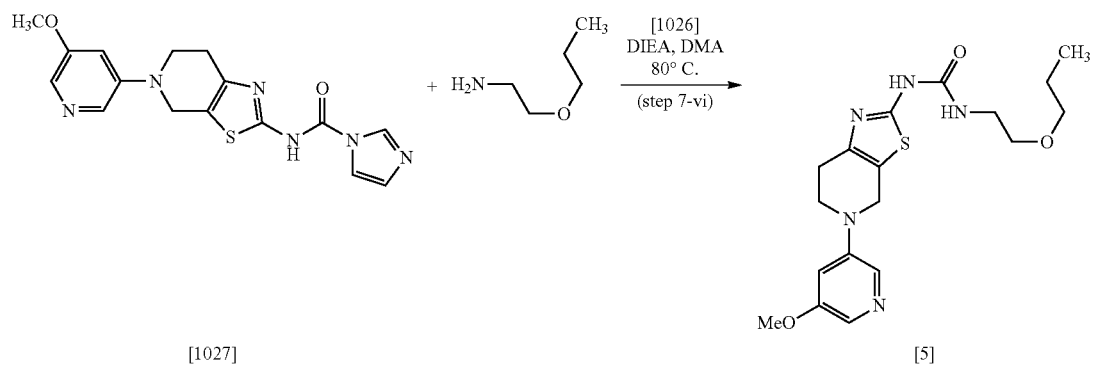

Example 8

Preparation of 4,5,6,7-tetrahydro-5-(5-methoxypyridin-3-yl)-N-(pyrazin-2-yl)thiazolo[5,4-c]pyridin-2-amine (Compound 18)

As shown in step 8-i of Scheme 8, to a solution of 5-(5-methoxypyridin-3-yl)-4,5,6,7-tetrahydrothiazolo[5,4-c]pyridin-2-amine (Compound 1026, 20 mg, 0.076 mmol) in NMP (1 mL) was added 2-fluoropyrazine (22.4 mg, 0.229 mmol) and $Cs_2CO_3$ (149 mg, 0.46 mmol). The reaction mixture was heated 110° C. for 18 h. The crude mixture was purified by medium pressure silica gel chromatography (0 to 10% MeOH in DCM) followed by a second purification using reversed-phase chromatography (5 to 90% $CH_3CN$/water). Fractions containing pure produce were brought to a neutral pH and the product isolated as the bis-HCl salt to give 4,5,6,7-tetrahydro-5-(5-methoxypyridin-3-yl)-N-(pyrazin-2-yl)thiazolo[5,4-c]pyridin-2-amine (Compound 18, 4 mg): ESMS (M+H) 341.13; $^1$H NMR ($CD_3OD$, 300 MHz) δ 8.65 (d, J=1.5 Hz, 1H), 8.51 (t, J=1.5 Hz, 1H), 8.41 (d, J=2.7 Hz, 1H), 8.22 (d, J=2.4 Hz, 1H), 7.96 (d, J=2.4 Hz, 1H), 7.69 (t, J=2.4 Hz, 1H), 4.67 (s, 2H), 4.04 (s, 3H), 3.98 (t, J=5.7 Hz, 2H), 3.01 (t, J=5.7 Hz, 2H) ppm.

Scheme 8

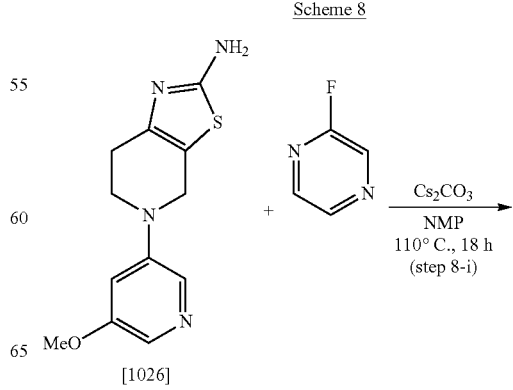

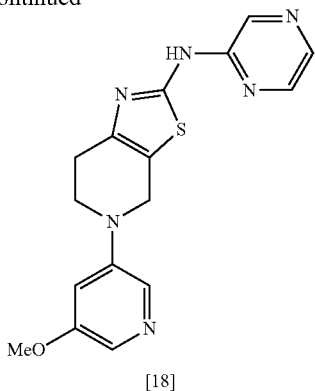

[18]

Example 9

Preparation of N-(4,5,6,7-tetrahydro-5-(5,6-dimethoxypyrazin-2-yl)thiazolo[5,4-c]pyridin-2-yl) acetamide (Compound 14)

As shown in step 9-i of Scheme 9, a 25% wt sodium methoxide (25 mL, 448.9 mmol) solution was added to 2,3-dichloropyrazine (7.2 g, 48.33 mmol) at ~5° C. The milky mixture was warmed to room temperature and stirred for 36 h. The reaction mixture was then diluted with DCM (50 mL), filtered, and the filtrate concentrated under reduced pressure. The residue was partitioned between DCM and 1:1 water/brine, the phases separated, the aqueous layer extracted with DCM, and the combined organics dried (MgSO$_4$), filtered, and concentrated to a liquid which crystallized on standing to provide 2,3-dimethoxypyrazine as a white crystalline material (Compound 1028, 5.56 g, 82%). ESMS (M+H) 141.00; $^1$H NMR (CDCl$_3$, 300 MHz) δ 7.61 (s, 2H), 4.00 (s, 6H) ppm.

As shown in step 9-ii of Scheme 9, N-bromosuccinimide (7.335 g, 41.21 mmol) was added to a solution of Compound 1028 (5.5 g, 39.25 mmol) in DMF (25 mL) at 0° C. and the resulting suspension was slowly warmed to room temperature overnight. Another 8.4 g of NBS was added and the solution was stirred for another 7 hours. The red reaction solution was then cooled to ~4° C. (ice bath), neutralized with 1N Na$_2$S$_2$O$_3$, and stirred for 30 minutes at 0° C. The resulting mixture was filtered and washed with warmed water (3×) to yield an off white solid, which was purified by medium pressure silica gel chromatography (0 to 20% EtOAc in Hexanes) to provide 5-bromo-2,3-dimethoxypyrazine (Compound 1029. 6.06 g (70%) as a white solid: ESMS (M+H) 218.94; $^1$H NMR (CDCl$_3$, 300 MHz) δ 7.72 (s, 1H), 4.04 (s, 3H), 4.00 (s, 3H) ppm.

As shown in step 9-iii of Scheme 9, a 250 mL flame dried round bottom flask was charged with 1,4-dioxa-8-azaspiro [4.5]decane (2.418 g, 2.140 mL, 16.89 mmol), Compound 1029 (3.7 g, 16.89 mmol), and 72 mL of 5:1 toluene:tBuOH. Palladium (II) acetate (189.6 mg, 0.8445 mmol) and XPhos (402.6 mg, 0.8445 mmol) were added and the reaction mixture was flushed with nitrogen gas for 90 min. Sodium t-butoxide (1.786 g, 18.58 mmol) was added and the reaction mixture was refluxed for 8 hours, followed by cooling to RT. The resulting crude dark reaction mixture was filtered, the filtrate was concentrated under reduced pressure, and the residue purified by medium pressure silica gel chromatography (0 to 25% EtOAc in hexanes) to yield 8-(5,6-dimethoxypyrazin-2-yl)-1,4-dioxa-8-azaspiro[4.5]decane (Compound 1030, 2.51 g, 53% yield) as a light yellow oil which crystallized on standing under high vacuum: ESMS (M+H) 282.13; $^1$H NMR (CDCl$_3$, 300 MHz) δ 7.12 (br s, 1H), 4.00 (s, 4H), 3.98 (s, 3H), 3.95 (s, 3H), 3.52 (m, 4H), 1.82 (m, 4H) ppm.

As shown in step 9-iv of Scheme 9, A suspension of Compound 1030 (2.46 g, 8.745 mmol) in 6N aq. HCl (43 mL) was stirred at room temperature for 2 hours. The crude reaction mixture was neutralizes at ~4° C. by the slow addition of 6N NaOH followed by the addition of 1N aq. K$_2$CO$_3$). The reaction was extracted with EtOAc (3×) and the combined organics dried (MgSO$_4$), followed by concentration under reduced pressure to give 1-(5,6-dimethoxypyrazin-2-yl)piperidin-4-one as an off white semi solid (Compound 1031, 1.51 g, 73%), which was used in the next step without further purification: $^1$H NMR (CDCl$_3$, 300 MHz) δ 7.33 (s, 1H), 4.07 (s, 3H), 4.04 (s, 3H), 3.86 (m, 4H), 2.62 (m, 4H) ppm.

As shown in step 9-v of Scheme 9, a 200 mL round bottom flask was charged with Compound 1031, pyrrolidine (1.45 g, 6.11 mmol), p-TsOH—H$_2$O (116.3 mg, 0.6112 mmol), and toluene:dichloroethane (15:12 mL). The mixture was heated at 80° C. over molecular sieves for 3 hours in a sealed Parr flask. After cooling, the mixture was filtered and the filtrate concentrated under reduced pressure. The residue was dissolved in dry MeOH (25 mL) and sulfur (215.6 mg, 6.723 mmol) was added in one portion. To the reaction mixture was added dropwise a solution of cyanamide (282.6 mg, 6.723 mmol) in dry MeOH (~10 mL) at 0° C. The reaction mixture was slowly warmed to room temperature and stirred overnight. The resulting dark red reaction mixture was concentrated under reduced pressure and directly purified by medium pressure silica gel chromatography (1:1 EtOAc in hexanes, then 100% EtOAc) to yield 5-(5,6-dimethoxypyrazin-2-yl)-4,5,6,7-tetrahydrothiazolo[5,4-c]pyridin-2-amine (Compound 1032, 230 mg, 55% yield) as a light brown solid: ESMS (M+H) 293.99.

As shown in step 9-vi of Scheme 9, to a solution of Compound 1032 (65.4 mg, 0.223 mmol) in DCM (2 mL) was added DIEA (200 μL, 1.148 mmol) and acetic anhydride (200 μL, 2.12 mmol). The reaction solution was stirred at room temperature for 150 min and the crude produce purified by medium pressure silica gel chromatography (10 to 80% EtOAc in Hexanes) to give N-(4,5,6,7-tetrahydro-5-(5,6-dimethoxypyrazin-2-yl)thiazolo[5,4-c]pyridin-2-yl)acetamide (Compound 14, 36.8 mg) as an off white solid, which was salted as its mono-mesylate salt to yield a beige solid: ESMS (M+H) 336.12; $^1$H NMR (300.0 MHz, DMSO-d$_6$) δ 7.31 (s, 1H), 4.55 (s, 2H), 3.91 (m, 3H), 3.83 (m, 5H), 2.73 (t, J=5.4 Hz, 2H), 2.39 (d, J=0.6 Hz, 3H) and 2.12 (s, 3H) ppm.

Scheme 9

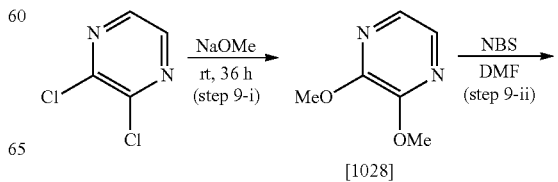

[1028]

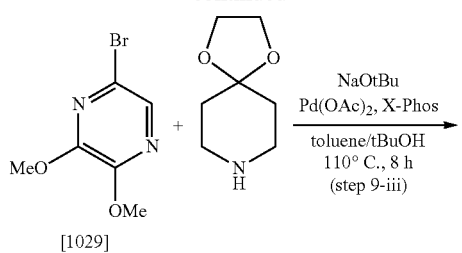

[1029]

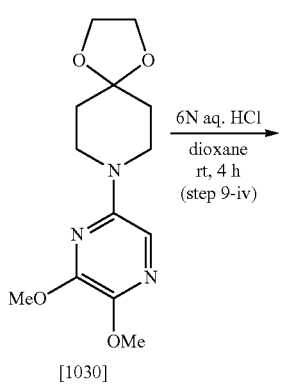

[1030]

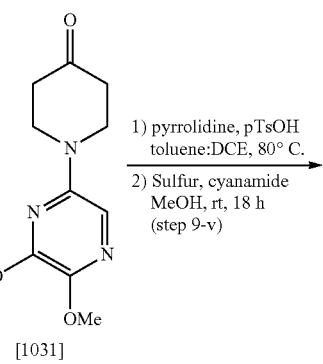

[1031]

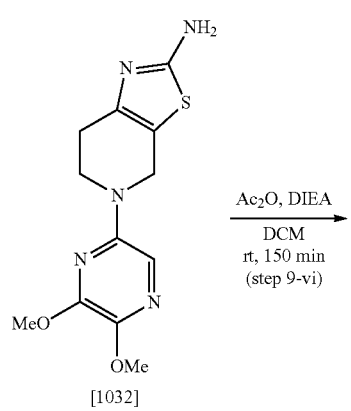

[1032]

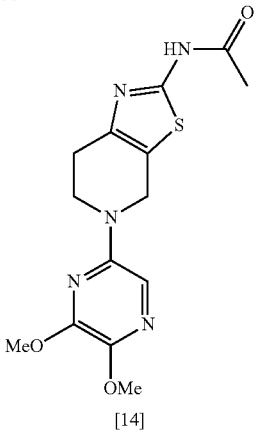

[14]

Using the appropriate bromophenyl, bromopyridine, or bromopyrazine for the step corresponding to step 9-iii and the appropriate acylating agent for the step corresponding to step 9-vi, the following compounds were similarly prepared: Compounds 2, 4, 7-9, 15, 17, 19, 21-33, 40, and 42-49.

Example 10

Preparation of N-(5-(pyrazin-2-yl)-4,5,6,7-tetrahydrothiazolo[5,4-c]pyridin-2-yl)acetamide (Compound 1)

As shown in step 10-i of Scheme 10, a mixture of tert-butyl 4-oxopiperidine-1-carboxylate (19.9 g), cyanamide (8.4 g) and sulfur (6.4 g) in pyridine (100 mL) was heated at 130° C. for 90 min. After cooling to RT, the resulting solid was collected by filtration and washed with ethyl ether (2×) to give tert-butyl 2-amino-6,7-dihydrothiazolo[5,4-c]pyridine-5(4H)-carboxylate (Compound 1033, 21.12 g).

As shown in step 10-ii of Scheme 10, to Compound 1033 (10.0 g) in pyridine (80 mL) was added acetyl chloride (4.2 mL). After stirring at 50° C. for 30 min, water (200 mL) was added. The resulting solid was collected by filtration and washed with water (2×) gave tert-butyl 2-acetamido-6,7-dihydrothiazolo[5,4-c]pyridine-5(4H)-carboxylate (Compound 1034, 10.873 g).

As shown in step 10-iii of Scheme 10, a solution of Compound 1034 (3.31 g) in methanol (50 mL) and 4N HCl-dioxane (40 mL) was heated at 50° C. for 30 minutes. Removal of the volatiles under reduced pressure gave N-(4,5,6,7-tetrahydrothiazolo[5,4-c]pyridin-2-yl)acetamide (Compound 1035) as the HCl salt.

As shown in step 10-iv of Scheme 10, to a solution of 50 mg of Compound 1035 in 3 mL of NMP was added 100 mg of 2-chloro pyrazine. The reaction mixture was warmed to 250° C. for 10 minutes under microwave irradiation. The reaction was poured into water (10 mL) and the crude product collected by filtration. The crude solid was purified by silica gel chromatography ($CH_2Cl_2$ to EtOH) to provide N-(5-(pyrazin-2-yl)-4,5,6,7-tetrahydrothiazolo[5,4-c]pyridin-2-yl)acetamide (Compound 1, 6.8 mg): ESMS (M+H) 276.16.

Scheme 10

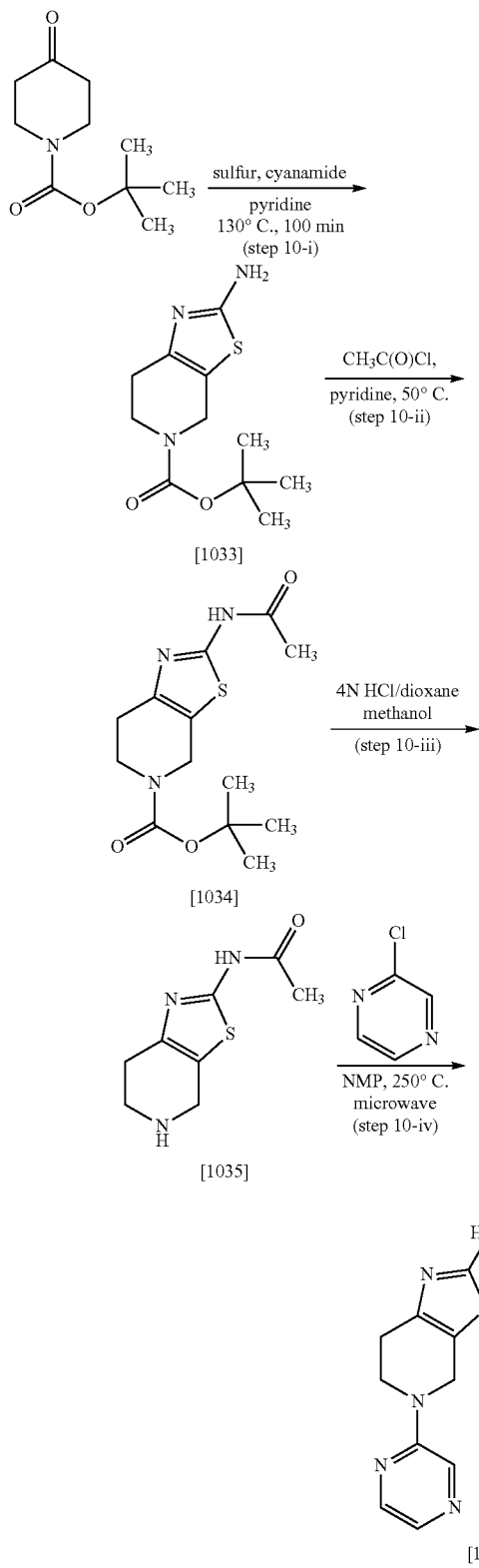

[1033]

[1034]

[1035]

[1]

Table 2 provides analytical characterization data for certain compounds of formula I (blank cells indicate that the test was not performed). Compound numbers in Table 2 correspond to those depicted in Table 1.

TABLE 2

| Compound No. | ESMS (M + H) | $^1$H NMR (300 MHz, unless indicated otherwise) NMR peaks given as δ values |
|---|---|---|
| 1 | 276.16 | |
| 2 | 310.40 | (DMSO-$d_6$): δ 8.39 (s, 1H), 7.90 (s, 1H), 4.75 (br s, 2H), 3.97 (dd, 2H), 2.76 (dd, 2H), 2.12 (s, 3H) |
| 3 | 334.05 | $^1$H NMR (methanol-$d_4$): δ 8.13 (d, J = 2.1 Hz, 1H), 7.88 (d, J = 2.1 Hz, 1H), 7.61 (d, J = 2.1 Hz, 1H), 4.59 (t, J = 1.5 Hz, 2H), 4.012 (s, 3H), 3.89 (t, J = 5.7 Hz, 2H), 3.28 (q, J = 7.2 Hz, 2H), 2.84 (m, 2H), 2.71 (s, 3H, MsOH), 1.17 (t, J = 7.2 Hz, 3H) ppm. |
| 4 | 335.00 | $^1$H NMR (methanol-$d_4$ with 2 drops of CDCl$_3$): δ 8.17 (d, J = 2.4 Hz, 1H), 7.88 (d, J = 2.1 Hz, 1H), 7.60 (t, J = 2.1 Hz, 1H), 4.67 (s, 2H), 4.22 (s, 2H), 4.03 (s, 3H), 3.95 (t, J = 5.7 Hz, 2H), 3.53 (s, 3H), 2.97 (m, 2H) ppm. |
| 5 | 392.00 | (CDCl$_3$): 8.04 (d, J = 2.4 Hz, 1H), 7.84 (d, J = 2.4 Hz, 1H), 6.75 (t, J = 2.4 Hz, 1H), 4.37 (s, 2H), 3.86 (s, 3H), 3.69 (t, J = 6 Hz, 2H), 3.54 (m, 4H), 3.43 (t, J = 6.6 Hz, 2H), 2.85 (t, J = 5.7 Hz, 2H) 1.60 (m, 2H), 0.93 (t, J = 7.5 Hz, 3H) ppm |
| 6 | 372.25 | (CDCl3): δ 8.66 (s, 1H), 8.41 (s, 1H), 7.52 (s, 1H), 7.26 (s, CDCl$_3$), 5.90 (s, 1H), 4.46 (s, 2H), 3.82 (t, J = 5.0 Hz, 2H), 3.35 (dd, J = 5.9, 7.1 Hz, 2H), 2.95-2.89 (m, 6H) and 1.21 (t, J = 7.2 Hz, 3H) ppm |
| 7 | 343.09 | (CDCl$_3$): δ 8.63 (d, J = 2.8 Hz, 1H), 8.35 (s, 1H), 7.63 (s, 1H), 4.56 (s, 2H), 3.86 (t, J = 5.7 Hz, 2H), 2.96 (t, J = 5.7 Hz, 2H), 2.88 (s, 3H) and 2.32 (s, 3H) ppm |
| 8 | 373.23 | (CDCl$_3$): δ 8.67 (s, 1H), 8.27 (s, 1H), 7.72 (s, 1H), 7.26 (s, CDCl3), 4.56 (s, 2H), 4.09 (s, 2H), 3.83 (t, J = 5.7 Hz, 2H), 3.44 (s, 3H), 2.89 (t, J = 5.7 Hz, 2H) and 2.78 (s, 3H) ppm |
| 9 | 335.10 | (DMSO-$d_6$): δ 7.47 (d, J = 2.3 Hz, 1H), 7.26 (d, J = 2.3 Hz, 1H), 4.41 (s, 2H), 3.83-3.78 (m, 6H), 3.64 (t, J = 5.7 Hz, 2H), 2.78 (t, J = 5.5 Hz, 2H), 2.39 (s, 3H) and 2.11 (s, 3H) ppm (Et2O present) |
| 10 | 364.27 | (DMSO-$d_6$): δ 7.52 (d, J = 2.2 Hz, 1H), 7.31 (d, J = 2.2 Hz, 1H), 6.89 (s, 1H), 4.41 (s, 2H), 3.81 (m, 6H), 3.67 (t, J = 5.7 Hz, 2H), 3.16 (q, J = 7.0 Hz, 2H), 2.79 (m, 2H), 2.73 (d, J = 0.3 Hz, H), 2.44 (s, 3H) and 1.08 (t, J = 7.1, 3H) ppm. |
| 11 | 398.22 | (DMSO-$d_6$): δ 7.42 (d, J = 2.3 Hz, 1H), 7.20 (d, J = 2.3 Hz, 1H), 6.90 (m, 1H), 4.33 (s, 2H), 3.79 (s, 6H), 3.70-3.66 (m, 2H), 3.58 (t, J = 5.7 Hz, 2H), 3.48 (t, J = 5.8 Hz, 2H), 2.72 (m, 2H) and 2.36 (s, 3H) ppm |
| 12 | 430.25 | (CDCl$_3$): δ 8.58 (d, J = 2.4 Hz, 1H), 8.40 (s, 1H), 7.44 (s, 1H), 7.26 (s, CDCl3), 6.17 (s, 1H), 4.42 (s, 2H), 3.78 (t, J = 5.6 Hz, 2H), 3.51 (dd, J = 4.7, 14.6 Hz, 4H), 3.39 (q, J = 6.6 Hz, 3H), 2.92 (d, J = 8.0 Hz, H), 2.88 (s, 3H), 1.59 (dd, J = 6.9, 14.2 Hz, 2H) and 0.91 (td, J = 7.4, 3.7 Hz, 3H) ppm |
| 13 | 346.00 | (CDCl$_3$): δ 8.04 (d, J = 3 Hz, 1H), 7.84 (d, J = 3 Hz, 1H), 6.75 (d, J = 3 Hz, 1H), 4.39 (s, 2H), 4.12 (t, J = 6 Hz, 4H), 3.86 (s, 3H), 3.69 (t, J = 6 Hz, 2H), 2.82 (m, 2H), 2.37 (m, 2H) ppm |
| 14 | 336.12 | (DMSO-$d_6$): δ 7.31 (s, 1H), 4.55 (s, 2H), 3.91 (m, 3H), 3.83 (m, 5H), 2.73 (t, J = 5.4 Hz, 2H), 2.39 (d, J = 0.6 Hz, 3H) and 2.12 (s, 3H) ppm |
| 15 | 321.09 | (DMSO-$d_6$): δ 8.45 (s, 1H), 7.95 (s, 1H), 7.37 (d, J = 2.4 Hz, 1H), 7.16 (d, J = 2.4 Hz, 1H), 4.35 (s, 2H), 3.79-3.73 (m, 6H), 3.57 (t, J = 5.7 Hz, 2H), 2.89 (s, H), 2.54 (s, 3H) and 2.32 (s, 3H) ppm |
| 16 | 422.29 | (CDCl$_3$): δ 7.38 (d, J = 2.4 Hz, 1H), 7.26 (s, CDCl3), 6.84 (d, J = 2.4 Hz, 1H), 6.15 (s, 1H), 4.20 (br s, 1H), 3.98 (s, 3H), 3.88 (s, 3H), 3.55-3.48 (m, 6H), 3.43-3.35 (m, 2H), 2.88 (s, 3H), 2.82 (t, J = 5.5 Hz, 2H), 1.63-1.55 (m, 2H) and 0.92 (t, J = 7.4 Hz, 3H) ppm |
| 17 | 344.27 | (CDCl$_3$): δ 8.39 (s, 1H), 8.19 (s, 1H), 7.26 (s, CDCl3), 4.78 (t, J = 1.8 Hz, 2H), 4.09-4.02 (m, 2H), 3.35 (t, J = 1.6 Hz, 1H), 2.94 (s, 2H) and 2.31 (s, 3H) ppm |
| 18 | 341.00 | (methanol-$d_4$): δ 8.65 (d, J = 1.5 Hz, 1H), 8.51 (t, J = 1.5 Hz, 1H), 8.41 (d, J = 2.7 Hz, 1H), 8.22 (d, J = 2.4 Hz, 1H), 7.96 (d, J = 2.4 Hz, 1H), 7.69 (t, J = 2.4 Hz, 1H), 4.67 (s, 2H), 4.04 (s, 3H), 3.98 (t, J = 5.7 Hz, 2H), 3.01 (t, J = 5.7 Hz, 2H) ppm |
| 19 | 323.00 | (methanol-$d_4$): δ 8.14 (s, 1H), 7.88 (d, 1H), 7.60 (d, J = 1.8 Hz, 1H), 5.15 (d, j = 1.5 Hz, 1H), 5.00 |

TABLE 2-continued

| Compound No. | ESMS (M + H) | ¹H NMR (300 MHz, unless indicated otherwise) NMR peaks given as δ values |
|---|---|---|
| 20 | 366.28 | (d, j = 1.5 Hz, 1H), 4.66 (s, 2H), 4.01 (s, 3H), 3.91 (t, J = 5.4 Hz, 2H), 2.91 (m, 2H) ppm. (CDCl₃): δ 8.83 (br s, 1H), 7.39 (d, J = 2.5 Hz, 1H), 7.26 (s, CDCl3), 6.88 (d, J = 2.4 Hz, 1H), 4.25 (br s, 2H), 3.98 (s, 3H), 3.88 (s, 3H), 3.83 (s, H), 3.55 (t, J = 5.7 Hz, 2H) and 2.89-2.87 (m, 5H) ppm |
| 21 | | (DMSO-d₆, 400 MHz): 2.29 (s, 3H), 3.10 (t, 2H), 3.88 (s, 3H), 3.89 (s, 3H), 4.03 (t, 2H), 6.83 (dd, 1H0, 6.88 (d, 1H), 6.91 (d, 1H), 9.0 (bs, 1H, D₂O exchangeable) |
| 22 | | (methanol-d₄, 400 MHz): δ 2.11 (s, 3H), 3.05 (t, 2H), 3.80 (s, 3H), 4.02 (t, 2H), 7.40 (t, 1H), 8.01 (d, 1H), 8.12 (d, 1H). |
| 23 | | (DMSO-d₆, 400 MHz): δ 11.98 (bs, 1H), 8.01 (s, 1H), 7.72 (s, 1H), 6.95 (s, 1H), 4.23 (s, 2H), 3.82 (s, 3H), 3.71 (t, 2H), 2.69 (t, 2H), 2.15 (s, 3H) |
| 24 | | (DMSO-d₆, 400 MHz): δ 11.98 (bs, 1H), 8.39 (s, 1H), 7.98 (d, 1H), 7.41 (d, 1H), 7.22 (m, 1H), 4.42 (s, 2H), 3.71 (t, 2H), 2.70 (t, 2H), 2.16 (s, 3H) |
| 25 | | (DMSO-d₆, 400 MHz): δ 11.99 (bs, 1H), 7.92 (s, 1H), 7.48 (s, 1H), 4.74 (s, 2H), 3.93 (t, 2H), 3.82 (s, 3H), 2.74 (t, 2H), 2.16 (s, 3H) |
| 26 | | (CDCl₃, 400 MHz): δ 9.12 (bs, 1H), 7.84 (s, 1H), 7.38 (d, 1H), 6.64 (d, 1H), 4.24 (s, 2H), 3.88 (s, 3H), 3.56 (t, 2H), 2.81 (t, 2H), 2.22 (s, 3H) |
| 27 | 334.28 | (CDCl₃, 400 MHz): δ 6.79 (d, J = 8.7 Hz, 1H), 6.64 (d, J = 2.6 Hz, 1H), 6.52 (dd, J = 2.7, 8.6 Hz, 1H), 4.29 (m, 2H), 3.86 (s, 3H), 3.84 (s, 3H), 3.55 (t, J = 5.7 Hz, 2H), 2.84 (t, J = 5.6 Hz, 2H), 2.25 (s, 3H) and 0.00 (s, H) |
| 28 | 468.42 | (DMSO-d₆): δ 12.01 (s, 1H), 8.85-8.81 (m, 1H), 8.64 (d, J = 4.7 Hz, 1H), 8.05-7.96 (m, 2H), 7.62-7.57 (m, 1H), 6.80 (d, J = 8.8 Hz, 1H), 6.70 (d, J = 2.6 Hz, 1H), 6.48 (dd, J = 2.7, 8.7 Hz, 1H), 4.28 (s, 2H), 3.75 (s, 3H), 3.67 (s, 3H), 3.61 (t, J = 6.4 Hz, 2H), 3.52 (t, J = 5.6 Hz, 2H), 2.73 (m, 2H) and 2.50 (m, 2H) |
| 29 | 304.00 | (DMSO-d₆): δ 11.99 (s, 1H), 7.10 ((dd, 1H), 6.61 (dd, 1H), 6.53 (dd, 1H), 6.36 (dd, 1H), 4.36 (brd s, 2H)—H2O, 3.71 (s, 3H), 3.62 (t, 2H), 3.29 (s, 1H), 2.70 (t, 2H), 2.11 (s, 3H) |
| 30 | 338.00 | (DMSO-d₆): δ 11.99 (s, 1H), 7.19 (d, 1H), 6.73 (d, 1H), 6.56 (dd, 1H), 4.42 (brd s, H2O), 3.84 (s, 3H), 3.66 (t, 2 H), 3.30 (s, 2H), 2.72 (t, 2H), 2.11 (s, 3H) |
| 31 | 472.00 | (DMSO-d₆): δ 12.15 (brd mult, 1H), 8.88 (t, 1H), 8.50 (d, 1H), 8.04 (m, 2H), 7,65 (m, 1H), 7.20 (d, 1H), 6.85 (d, 1H), 6.60 (dd, 1H), 4.5 (s, 2H), 3.85 (s, 3H), 3.68 (t, 2H), 3.61 ((quart, 2H), 2.76 (m, 4H) |
| 32 | 469.81 | (DMSO-d₆): δ 12.03 (s, 1H), 8.85 (t, J = 5.8 Hz, 1H), 8.64 (d, J = 4.6 Hz, 1H), 8.05-7.97 (m, 2H), 7.63-7.58 (m, 1H), 7.37 (d, J = 2.3 Hz, 1H), 7.15 (d, J = 2.3 Hz, 1H), 4.34 (s, 2H), 3.78 (d, J = 1.3 Hz, 6H), 3.65-3.55 (m, 4H), 2.74 (t, J = 6.8 Hz, 4H) and 2.32 (s, 2H) |
| 33 | 455.36 | (DMSO-d₆): δ 12.13 (s, 1H), 9.07-9.03 (m, 1H), 8.69 (d, J = 4.5 Hz, 1H), 8.05-8.00 (m, 2H), 7.64 (dd, J = 2.1, 11.4 Hz, 1H), 7.35 (d, J = 2.3 Hz, 1H), 7.13 (d, J = 2.3 Hz, 1H), 4.32 (s, 2H), 4.28-4.17 (m, 2H), 3.73 (s, 6H), 3.53 (m, 2H), 2.73 (s, 2H) and 2.28 (s, 2H) |
| 34 | 454.00 | |
| 35 | 398.00 | |
| 36 | 498.00 | (DMSO-d₆): δ 10.6 (br m, 1H), 9.15 (s, 1H), 7.71 (d, 1H), 7.57 (d, 1H), 7.17 (d, 1H), 7.17 (m, 1H), 4.77 (m, 2H), 4.5 (s, 2H), 3.9 (s, 3H), 3.7 (t, 2H), 3.41 (dt, 2H), 2.85 (t, 2H), 2.68 (m, 2H) |
| 37 | 425.00 | (DMSO-d₆): δ 10.2 (br m, 1H), 7.7 (d, 1H), 7.16 (d, 1H) 7.13 (m, 1H), 4.4 (s, 2H), 3.9 (s, 3H), 3.7, dt, 2H), 3.2 (dt, 2H), 3.02 (dt, 2H), 2.74 (d, 6H), 2.73 (m, 2H), 1.8 (m, 2H) |
| 38 | 480.00 | (DMSO-d₆): δ 10.7 (br m, 1H), 9.12 (s, 1H), 7.7 (d, 1H), 7.6 (s, 1H), 7.1 (m, 2H), 4.89 (t, 2H), 4.75 (t, 2H), 4.45 (t, 2H), 4.40 (s, 1H), 3.9 (s, 3H), 3.7, (t, 2H) 2.87 (t, 2H), 2.6 (t, 2H) |
| 39 | 426.00 | |
| 40 | 422.43 | (DMSO-d₆): δ 12.1 (s, 1H), 9.0 (m, 1H), 8.73 (m, 1H), 7.72 (d, J = 2.5 Hz, 1H), 7.18 (d, J = 2.4 Hz, 1H), 4.49 (s, 2H), 3.84 (s, 3H), 3.74 (t, J = 5.5 Hz, 2H), 3.21 (d, J = 12.6 Hz, 2H), 2.85 (q, J = 11.8 Hz, 2H), 2.74 (br. s, 2H), 2.40 (d, J = 6.9 Hz, 2H), 2.15-2.00 (m, 1H), 1.77 (d, J = 13.7 Hz, 2H), 1.45 (q, J = 12.1 Hz, 2H) |
| 41 | 397.43 | (methanol-d₄): δ 7.77 (d, J = 2.4 Hz, 1H), 7.30 (d, J = 2.4 Hz, 1H), 4.56 (brS, 2H), 3.98 (s, 3H), 3.79 (m, 4H), 3.53 (q, J = 7.2 Hz, 2H), 2.91 (m, 2H), 2.80 (t, J = 6.0 Hz, 2H), 1.16 (t, J = 6.9 Hz, 3H) |
| 42 | 383.40 | (methanol-d₄): δ 7.78 (d, J = 2.4 Hz, 1H), 7.32 (d, J = 2.4 Hz, 1H), 4.56 (brS, 2H), 4.02 (s, 3H), 3.88 (t J = 5.7 Hz,, 2H), 3.75 (t, J = 6.0 Hz, 2H), 3.00 (m, 2H), 2.81 (t, J = 5.7 Hz, 2H) |
| 43 | 397.41 | (methanol-d₄): δ 7.78 (d, J = 2.4 Hz, 1H), 7.32 (d, J = 2.4 Hz, 1H), 4.56 (brS, 2H), 3.98 (s, 3H), 3.84 (t J = 5.7 Hz,, 2H), 3.75 (t, J = 6.0 Hz, 2H), 3.36 (s, 3H), 2.91 (m, 2H), 2.80 (t, J = 6.0 Hz, 2H) |
| 44 | 410.42 | |
| 45 | 464.41 | (DMSO-d₆): δ 12.0 (br. s, 1H), 7.73 (d, J = 2.5 Hz, 1H), 7.18 (d, J = 2.5 Hz, 1H), 4.49 (s, 2H), 4.32 (q, J = 12.9 Hz, 2H), 3.84 (s, 3H), 3.79-3.70 (m, 3H), 3.00 (t, J = 11.4 Hz, 1H), 2.73 (br. s, 2H), 2.37 (d, J = 7.0 Hz, 2H), 2.04-1.97 (br. s, 4H), 1.68-1.60 (m, 2H), 1.18-0.94 (m, 2H) |
| 46 | 450.44 | (DMSO-d₆): δ 12.0 (br. s, 1H), 7.73 (d, J = 2.5 Hz, 1H), 7.17 (d, J = 2.4 Hz, 1H), 4.49 (s, 2H), 4.37 (d, J = 13.1 Hz, 1H), 3.89 (s, 3H), 3.90-3.80 (m, 1H), 3.72 (t, J = 5.6 Hz, 2H), 3.09-3.01 (m, 1H), 2.75-2.67 (m, 3H), 2.60 (m, 1H), 2.03 (s, 3H), 2.0 (m, 1H), 1.85-1.78 (m, 2H), 1.63-1.39 (m, 2H) |
| 47 | 436.42 | (DMSO-d₆): δ 12.3 (br. s, 1H), 7.73 (d, J = 2.5 Hz, 1H), 7.18 (d, J = 2.4 Hz, 1H), 4.50 (s, 2H), 3.88 (s, 3H), 3.76-3.68 (m, 2H), 3.63-3.21 (m, 5H), 2.75 (br. s, 2H), 2.24-2.06 (m, 2H), 1.97 (s, 3H) |
| 48 | 436.44 | (DMSO-d₆): δ 12.3 (br. s, 1H), 7.73 (d, J = 2.5 Hz, 1H), 7.18 (d, J = 2.5 Hz, 1H), 4.50 (s, 2H), 3.84 (s, 3H), 3.76-3.68 (m, 2H), 3.63-3.21 (m, 5H), 2.75 (br. s, 2H), 2.24-2.06 (m, 2H), 1.97 (s, 3H) |
| 49 | 422.39 | (DMSO-d₆): δ 12.20 (br. s, 1H), 7.73 (d, J = 2.5 Hz, 1H), 7.18 (d, J = 2.5 Hz, 1H), 4.51 (s, 2H), 4.31-4.18 (m, 2H), 3.96 (t, J = 9.2 Hz, 1H), 3.84 (s, 3H), 3.74 (t, J = 5.6 Hz, 2H), 3.64-3.57 (m, 1H), 2.74 (br. s, 2H), 1.76 (s, 3H) |
| 50 | 398.00 | (DMSO-d₆): δ 10. (br m, 1H), 7.72 (d, 1H), 7.16 (d, 1H), 6.8 (br t, 1H), 4.27 (s, 2H), 3.88 (s, 3H), 3.7 (t, 2H), 3.44 (t, 2H), 3.33 (dt, 2H), 3.17 (m, 2H), 1.6 0 (quin, 2H) |
| 51 | 410.00 | (DMSO-d₆): δ 7.72 (d, 2H), 7.16 (d, 1H), 4.45 (s, 2H), 4.17 (m, 3H), 3.9 (s, 3H), 3.78 (m, 2H), 3.70 (t, 2H), 3.2 (s, 3H), 2.72 (t, 2H) |
| 52 | 440.00 | |
| 53 | 408.40 | (DMSO-d₆): δ 12.3 (br. s, 1H), 9.32 (br. s, 1H), 9.13 (br. s, 1H), 7.73 (d, J = 2.3 Hz, 1H), 7.18 (d, J = 2.3 Hz, 1H), 4.50 (s, 2H), 3.89 (s, 3H), 3.84-3.72 (m, 3H), 3.17-3.13 (m, 2H), 3.07-2.92 (m, 2H), 2.76 (br. s, 2H), 2.18-2.08 (m, 1H), 1.95-1.79 (m, 2H), 1.59 (qd, J = 8.6, 12.5 Hz, 1H) |
| 54 | 450.39 | (DMSO-d₆): δ 12.2 (m, 1H), 7.73 (d, J = 2.2 Hz, 1H), 7.18 (d, J = 2.1 Hz, 1H), 4.50 (s, 2H), 4.27 (m, 1H), 3.89 (s, 3H), 3.73 (t, J = 5.3 Hz, 2H), 3.50-3.24 (m, 2H), 3.17 (s, 2H), 2.88 (dd, J = 3.8, 14.8 Hz, 1H), 2.75 (br. s, 2H), 1.94 (s, 3H), 1.90-1.75 (m, 3H) |
| 55 | 408.00 | (DMSO-d₆): δ 7.72 (d, 1H), 7.16 (d, 1H), 4.42 (s, 2H), 3.88 (s, 3H), 3.70 (t, 2H), 3.58 (m, 4H), 3.48 (m, 4H), 2.71 (m2H) |
| 56 | 408.00 | (DMSO-d₆): δ 7.72 (d, 1H), 7.16 (d, 1H), 4.42 (s, 2H), 3.89 (s, 3H), 3.71 (t, 2H), 3.45 (m, 4H), 2.70 ((m, 2H), 1.55 (m, 2H), 1.65 (m, 4H) |
| 57 | 394.00 | |
| 58 | 426.00 | |
| 59 | 452.00 | |

Biological Assay of Compounds of the Invention

Example 11

PI3K Inhibition Assay

Using a Biomek FX from Beckman Coulter, 1.5 μL of each of ten 2.5-fold serial dilutions of a compound of the invention in 100% DMSO was added to an individual well (hereafter, "test well") in a 96 well polystyrene plate [Corning, Costar Item No. 3697]. One test well also contained 1.5 μL of DMSO with no compound. Another well contained an inhibitor in DMSO at a concentration known to completely inhibit the enzyme, (hereafter "background well"). Using a Titertek Multidrop, 50 μL of Reaction Mix [100 mM HEPES pH 7.5, 50 mM NaCl, 10 mM DTT, 0.2 mg/mL BSA, 60 μM phosphatidylinositol(4,5)-bisphosphate diC16 (PI(4,5)P$_2$; Avanti Polar Lipids, Cat. No. 840046P) and PI3K isoform of interest (see Table 3 for isoform concentrations)] was added to each well. To initiate the reaction, 50 μL of ATP Mix [20 mM MgCl$_2$, 6 μM ATP (100 μCi/μmole $^{33}$P-ATP)] was added each well, followed by incubating the wells for 30 min. at 25° C. Final concentrations in each well were 50 mM HEPES 7.5, 10 mM MgCl$_2$, 25 mM NaCl, 5 mM DTT, 0.1 mg/mL BSA, 30 μM PI(4,5)P$_2$, 3 μM ATP, and the PI3K isoform of interest (see Table 3). Final compound concentrations in each well ranged from 10 μM to 1 nM.

TABLE 3

| PI3K Isoform Concentrations | PI3K-α | PI3K-β | PI3K-γ | PI3K-δ |
|---|---|---|---|---|
| Enzyme concentration in Reaction Mix | 4 nM | 20 nM | 4 nM | 4 nM |
| Final enzyme concentration | 2 nM | 10 nM | 2 nM | 2 nM |

After incubation, the reactions in each well were quenched by addition of 50 μL of stop solution [30% TCA/Water, 10 mM ATP]. Each quenched reaction mixture was then transferred to a 96 well glass fiber filter plate [Corning, Costar Item No. 3511]. The plate was vacuum-filtered and washed three times with 150 μL of 5% TCA/water in a modified Bio-Tek Instruments ELX-405 Auto Plate Washer. 50 μL of scintillation fluid was added to each well and the plate read on a Perkin-Elmer TopCount™ NXT liquid scintillation counter to obtain $^{33}$P-counts representing inhibition values.

The value for the background well was subtracted from the value obtained for each test well and the data were fit to the competitive tight binding Ki equation described by Morrison and Stone, *Comments Mol. Cell Biophys.* 2: 347-368, 1985.

Each of compounds 1 to 59 has a K$_i$ of less than 1.0 micromolar for PI3Kγ. Each of compounds 3, 3-12, 14-19, 23, 25, 32-39, 44, 50-52, and 57 has a K$_i$ of less than 0.10 micromolar for PI3Kγ. Each of compounds 5, 9, 12, 14, 25, 36, and 52 has a K$_i$ of less than 0.020 micromolar for PI3Kγ. For example, compound 52 has a K$_i$ of 0.003 micromolar.

All publications and patents cited in this specification are herein incorporated by reference as if each individual publication or patent were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula:

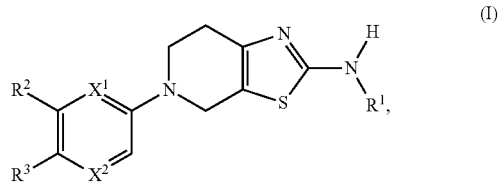

or a pharmaceutically acceptable salt thereof, wherein:

each of $X^1$ and $X^2$ is, independently, N or CH;

$R^1$ is —C(O)H, —C(O)R$^{1a}$, —C(O)N(R$^{1a}$)(R$^{1b}$), or a 5- or 6-membered heteroaryl ring having 1-3 heteroatoms selected from N, O, or S and optionally substituted with 1, 2 or 3 J$^{R2}$ groups;

$R^{1a}$ is C$_{1-6}$ aliphatic, C$_{3-6}$ cycloaliphatic, azetidinyl, pyrrolidinyl, or piperidinyl, wherein R$^{1a}$ is optionally substituted with 1, 2, 3, or 4, occurrences of J$^R$;

$R^{1b}$ is hydrogen, C$_{1-4}$ aliphatic, or R$^{1a}$ and R$^{1b}$, together with the nitrogen to which they are attached, form a 4-6 membered heterocyclic ring, wherein said heterocyclic ring of R$^{1a}$ and R$^{1b}$ optionally comprises one additional heteroatom selected from nitrogen and oxygen, and wherein said heterocyclic ring of R$^{1a}$ and R$^{1b}$ is optionally substituted with 1 or 2 J$^{R2}$ groups;

each J$^R$ is independently fluoro, oxo, —C(O)J$^{R1}$, —C(O)N(J$^{R1}$)$_2$, —C(O)O(J$^{R1}$), —N(J$^{R1}$)C(O)J$^{R1}$, —OJ$^{R1}$, —SJ$^{R1}$, phenyl or a 5-6 membered heteroaryl or heterocyclyl having up to 2 atoms selected from nitrogen, oxygen, or sulfur, wherein said phenyl, heteroaryl, or heterocyclyl or J$^R$ is optionally substituted with 1 or 2 J$^{R2}$ groups;

each J$^{R1}$ is independently selected from hydrogen, C$_{1-4}$aliphatic, C$_{3-6}$cycloaliphatic, phenyl, benzyl, heterocyclyl, or heteroaryl, wherein said heterocyclyl of J$^{R1}$ is a 5- or 6-membered ring having 1 or 2 atoms selected from N, or O, said heteroaryl of R$^2$ is a 5- or 6-membered monocyclic ring or a 9- or 10-membered fused bicyclic ring system having 1, 2, or 3 atoms selected from N, O, or S, and each of said aliphatic, cycloaliphatic, phenyl, benzyl, heterocyclyl, or heteroaryl of J$^{R1}$ is optionally substituted with up to three J$^{R2}$ groups;

each J$^{R2}$ is selected from chloro, fluoro, oxo, C$_{1-2}$alkyl, C$_{1-2}$alkyl substituted with 1-3 fluorine atoms, C$_{3-6}$cycloalkyl, —OH, —OC$_{1-2}$alkyl, —OC$_{1-2}$alkyl substituted with 1-3 fluorine atoms, —C(O)C$_{1-2}$alkyl, or —SC$_{1-2}$alkyl;

$R^2$ is hydrogen, fluoro, chloro, C$_{1-6}$aliphatic, —OC$_{1-6}$aliphatic, C$_{3-6}$cycloaliphatic, —OC$_{3-6}$cycloaliphatic, cyano, —NH$_2$, —NHC$_{1-6}$aliphatic, —NHC$_{3-6}$cycloaliphatic, —NHS(O)$_2$C$_{1-6}$aliphatic, —NHS(O)$_2$C$_{3-6}$cycloaliphatic, —NHS(O)$_2$phenyl, —NHS(O)$_2$benzyl, —NHS(O)$_2$heteroaryl, —S(O)$_2$C$_{1-6}$aliphatic, —S(O)$_2$C$_{3-6}$cycloaliphatic, —S(O)$_2$phenyl, —S(O)$_2$benzyl, —S(O)$_2$heteroaryl, —S(O)$_2$NHC$_{1-6}$aliphatic, —S(O)$_2$NHC$_{3-6}$cycloaliphatic, —S(O)$_2$NHphenyl, —S(O)$_2$NHbenzyl, or —S(O)$_2$NHheteroaryl, wherein said heteroaryl of R$^2$ is a 5- or 6-membered ring having 1, 2, or 3 atoms selected from N, O, or S, and wherein said aliphatic, cycloaliphatic, phenyl, benzyl, or heteroaryl of R$^2$ is optionally substituted with 1, 2, or 3 J$^{R2}$ groups; and R³ is hydrogen, fluoro, chloro, C$_{1-3}$aliphatic, —OC$_{1-3}$aliphatic, NH$_2$, or NHC$_{1-3}$aliphatic, wherein said aliphatic of R³ is optionally substituted with up to 3 occurrences of fluoro.

2. The compound according to claim 1, or a pharmaceutically acceptable salt thereof, wherein:
each of X¹ and X² is N or X¹ is CH and X² is N;
R¹ is —C(O)H, —C(O)R$^{1a}$, —C(O)N(R$^{1a}$)(R$^{1b}$), or a 6-membered heteroaryl ring having up to 2 nitrogen atoms and optionally substituted with 1, 2 or 3 J$^{R2}$ groups;
R$^{1a}$ is C$_{1-4}$ aliphatic, azetidinyl, pyrrolidinyl, or piperidinyl, wherein R$^{1a}$ is optionally substituted with 1, 2, or 3 occurrences of J$^R$;
R$^{1b}$ is hydrogen or R$^{1a}$ and R$^{1b}$, together with the nitrogen to which they are attached, form a 4-6 membered heterocyclic ring, wherein said heterocyclic ring of R$^{1a}$ and R$^{1b}$ optionally comprises one additional heteroatom selected from nitrogen and oxygen, and wherein said heterocyclic ring of R$^{1a}$ and R$^{1b}$ is optionally substituted with 1 or 2 J$^{R2}$ groups;
each J$^R$ is independently fluoro, oxo, —C(O)J$^{R1}$, —C(O)N(J$^{R1}$)$_2$, —C(O)O(J$^{R1}$), N(J$^{R1}$)C(O)J$^{R1}$, —OJ$^{R1}$, phenyl, or a 5-6 membered heteroaryl or heterocyclyl having up to 2 atoms selected from nitrogen, oxygen, or sulfur, wherein said phenyl, heteroaryl, or heterocyclyl or J$^R$ is optionally substituted with 1 or 2 J$^{R2}$ groups;
each J$^{R1}$ is independently selected from hydrogen, C$_{1-4}$aliphatic, C$_{3-6}$cycloaliphatic, phenyl, benzyl, heterocyclyl, or heteroaryl, wherein said heterocyclyl of J$^{R1}$ is a 5- or 6-membered ring having 1 or 2 atoms selected from N, or O, said heteroaryl of R² is a 5- or 6-membered monocyclic ring having 1, 2, or 3 atoms selected from N, O, or S, and each of said aliphatic, cycloaliphatic, phenyl, benzyl, heterocyclyl, or heteroaryl of J$^{R1}$ is optionally substituted with up to three J$^{R2}$ groups;
each J$^{R2}$ is selected from chloro, fluoro, oxo, C$_{1-2}$alkyl, C$_{1-2}$alkyl substituted with 1-3 fluorine atoms, C$_{3-6}$cycloalkyl, —OH, —OC$_{1-2}$ alkyl, —OC$_{1-2}$alkyl substituted with 1-3 fluorine atoms, —C(O)C$_{1-2}$ alkyl, or —SC$_{1-2}$alkyl;
each of R² and R³ is, independently hydrogen, chloro, trifluoromethyl or —OCH$_3$, wherein at least one of R² and R³ is not hydrogen.

3. The compound according to claim 1, or a pharmaceutically acceptable salt thereof, wherein R¹ is selected from

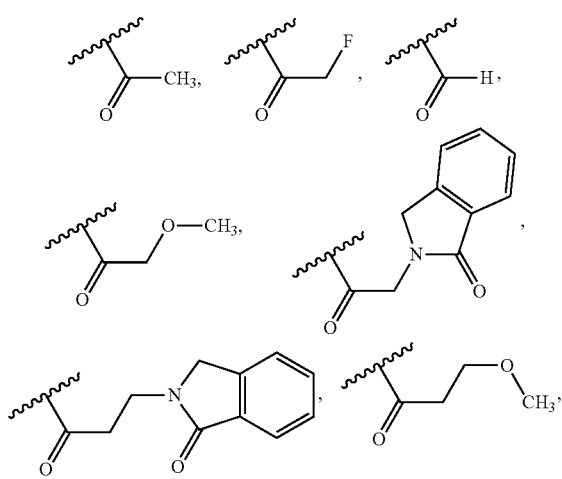

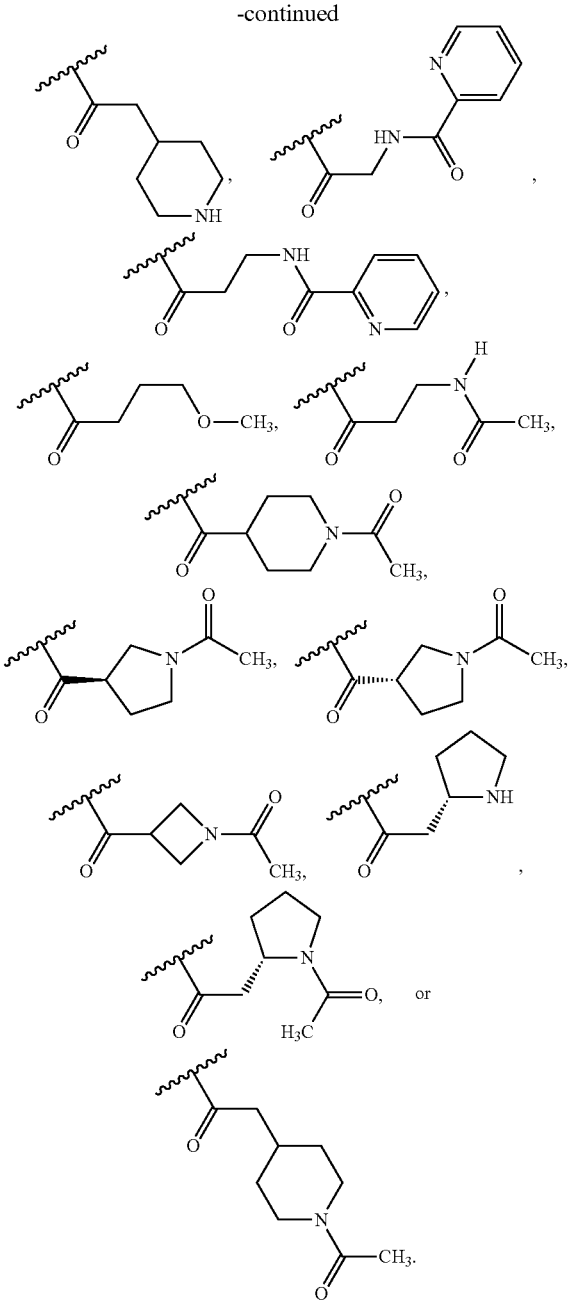

4. The compound according to claim 1, or a pharmaceutically acceptable salt thereof, wherein R¹ is —C(O)N(R$^{1a}$)(R$^{1b}$).

5. The compound according to claim 1, or a pharmaceutically acceptable salt thereof, wherein R$^{1b}$ is hydrogen and R$^{1a}$ is a C$_{1-4}$ aliphatic optionally substituted with —OJ$^{R1}$, —SJ$^{R1}$, or a 5-6 membered heteroaryl having up to 2 atoms selected from nitrogen or oxygen and optionally substituted with up to two J$^{R2}$ groups.

6. The compound according to claim 1, or a pharmaceutically acceptable salt thereof, wherein R$^{1a}$ and R$^{1b}$, together with the nitrogen to which they are attached, form a 4-6 membered heterocyclic ring, wherein said heterocyclic ring optionally comprises one additional heteroatom selected from nitrogen and oxygen, and wherein said heterocyclic ring is optionally substituted with 1 or 2 J$^{R2}$ groups.

7. The compound according to claim 1, or a pharmaceutically acceptable salt thereof, wherein R¹ is selected from

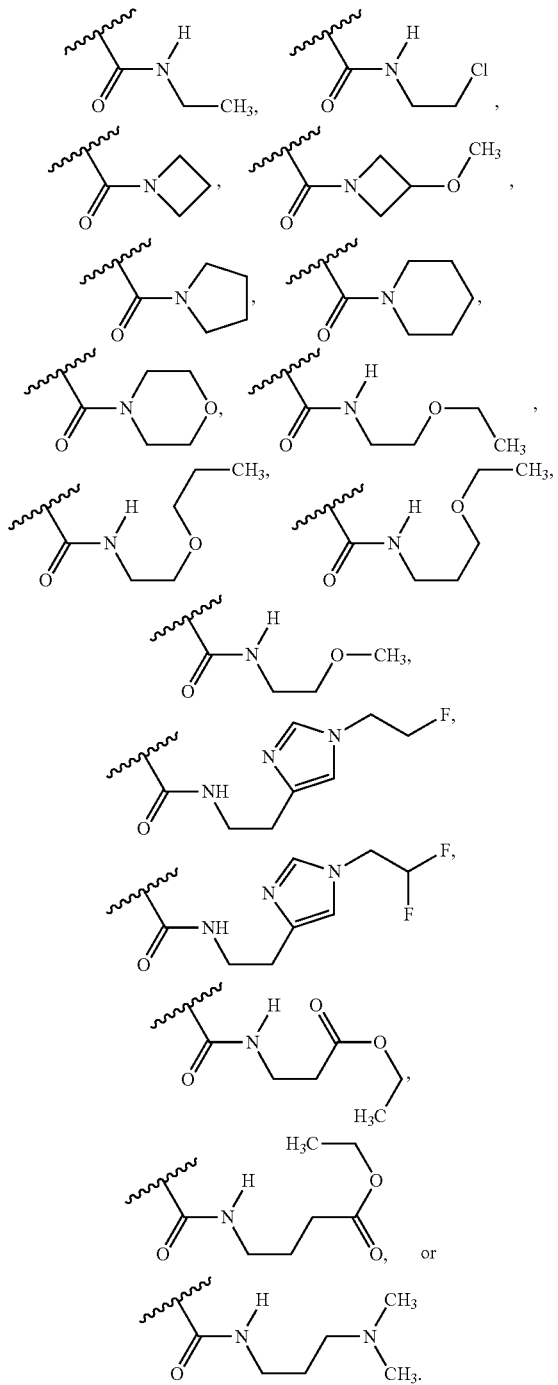

8. The compound according to claim 1, or a pharmaceutically acceptable salt thereof, wherein each of X¹ and X² is N.

9. The compound according to claim 1, or a pharmaceutically acceptable salt thereof, wherein X¹ is CH and X² is N.

10. The compound according to claim 1, wherein R² is —OC₁₋₃ alkyl or —CF₃.

11. The compound according to claim 1, or a pharmaceutically acceptable salt thereof, wherein

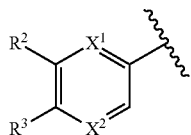

is selected from:

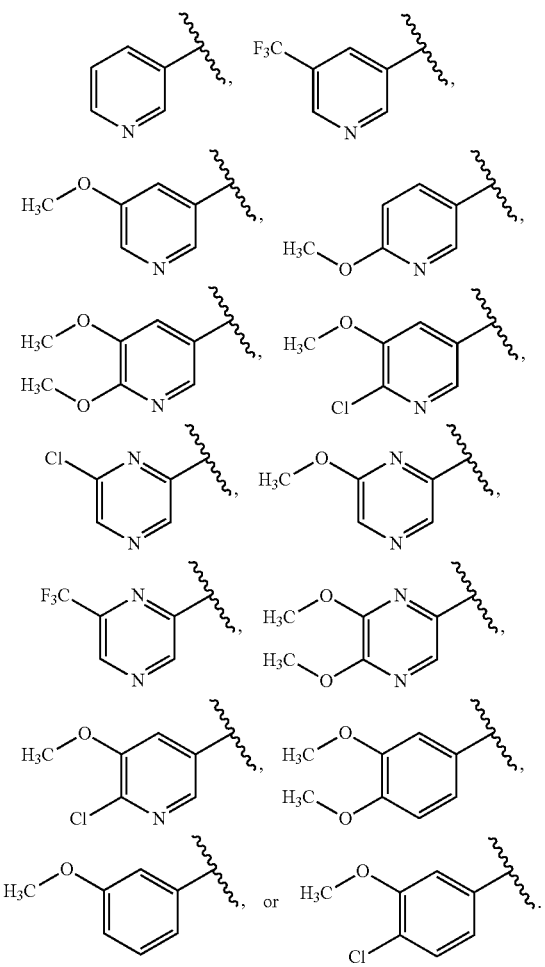

12. The compound according to claim 1, or a pharmaceutically acceptable salt thereof, wherein said compound is selected from

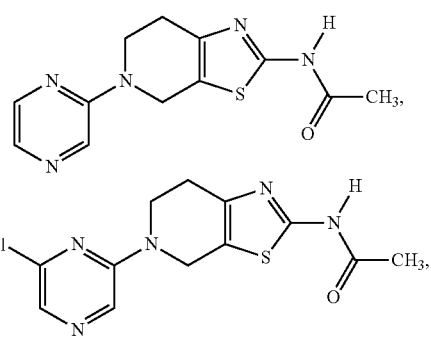

-continued

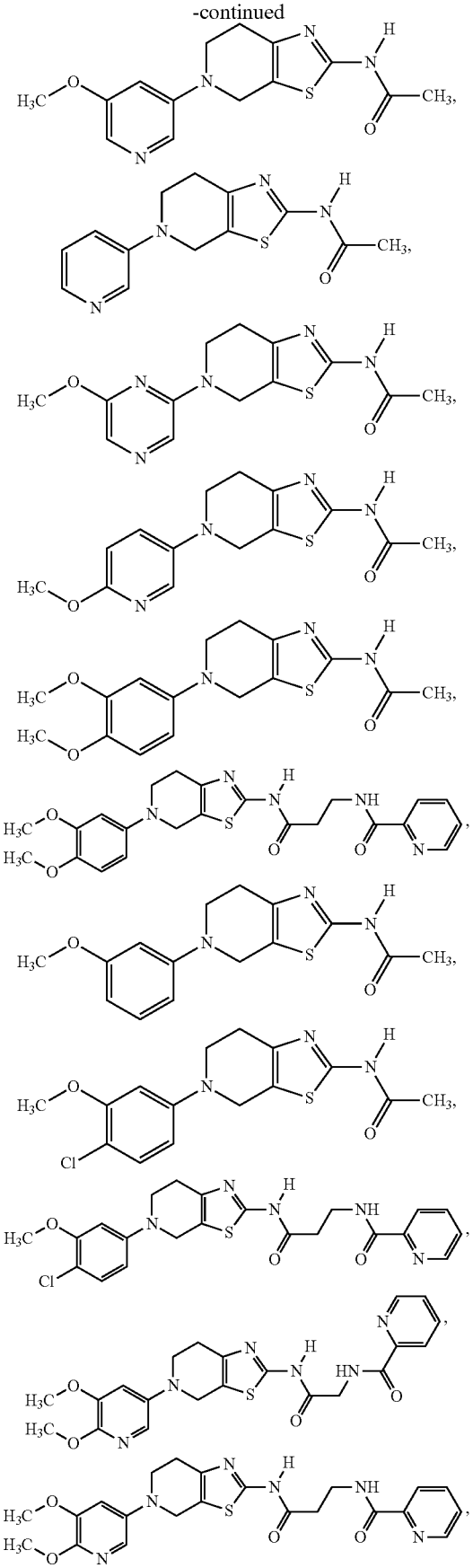
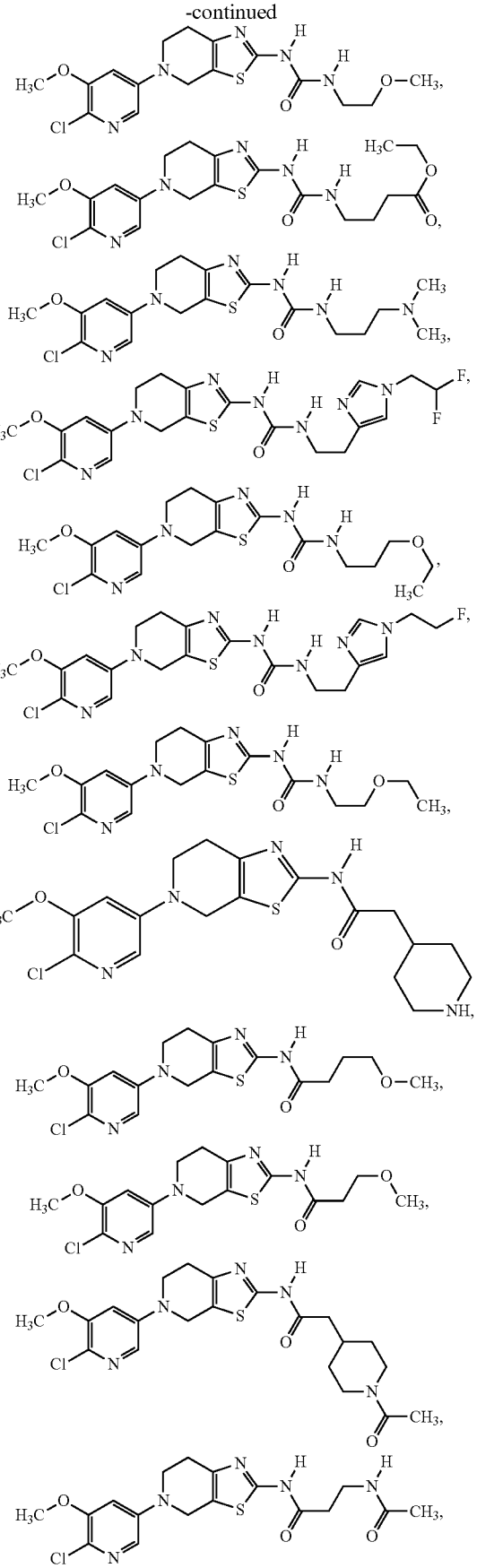

-continued
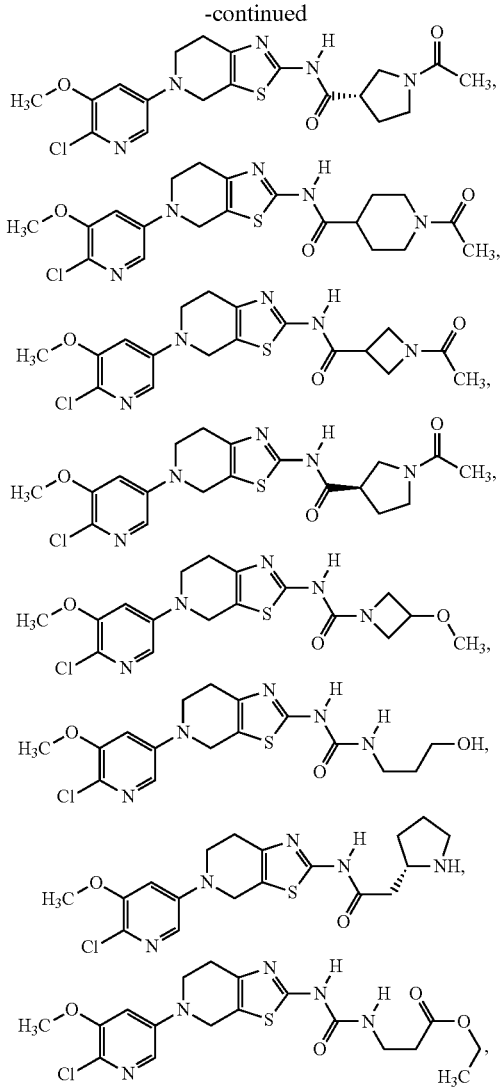
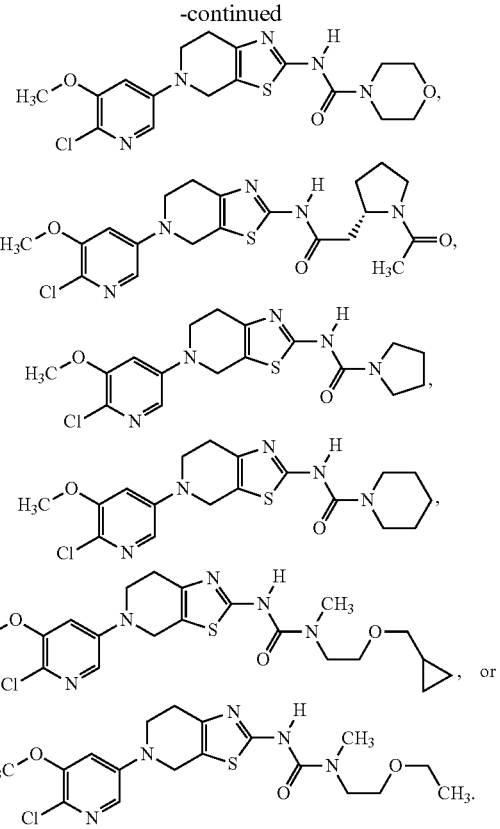
13. A pharmaceutical composition comprising a compound according to claim 1 and a pharmaceutically acceptable carrier, adjuvant, or vehicle.
14. A method of inhibiting PI3K-gamma kinase activity in a biological sample comprising contacting said biological sample with a compound according to claim 1 or a composition according to claim 13.
* * * * *